(12) United States Patent
Pancer et al.

(10) Patent No.: US 10,036,747 B2
(45) Date of Patent: Jul. 31, 2018

(54) LAMBODIES WITH HIGH AFFINITY AND SELECTIVITY FOR GLYCANS AND USES THEREFOR

(71) Applicant: UNIVERSITY OF MARYLAND, BALTIMORE, Baltimore, MD (US)

(72) Inventors: Zeev Pancer, Baltimore, MD (US); Li Mao, Clarksville, MD (US); Xia Hong, Olney, MD (US); Mark Z. Ma, Ellicott City, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 31 days.

(21) Appl. No.: 14/359,653

(22) PCT Filed: Nov. 21, 2012

(86) PCT No.: PCT/US2012/066413
§ 371 (c)(1),
(2) Date: May 21, 2014

(87) PCT Pub. No.: WO2013/078425
PCT Pub. Date: May 30, 2013

(65) Prior Publication Data
US 2014/0322825 A1 Oct. 30, 2014

Related U.S. Application Data

(60) Provisional application No. 61/701,234, filed on Sep. 14, 2012, provisional application No. 61/703,517, filed on Sep. 20, 2012, provisional application No. 61/562,575, filed on Nov. 22, 2011.

(51) Int. Cl.
*G01N 33/566* (2006.01)
*G01N 33/53* (2006.01)
*G01N 33/574* (2006.01)
*C07K 14/46* (2006.01)

(52) U.S. Cl.
CPC ......... *G01N 33/566* (2013.01); *C07K 14/461* (2013.01); *G01N 33/5308* (2013.01); *G01N 33/574* (2013.01); *C07K 2319/70* (2013.01); *G01N 2400/02* (2013.01)

(58) Field of Classification Search
CPC .. C07K 14/461; C07K 2319/70; G01N 33/68; G01N 33/566; G01N 33/5308; G01N 33/574; G01N 2400/02
See application file for complete search history.

(56) References Cited

U.S. PATENT DOCUMENTS

| | | | | |
|---|---|---|---|---|
| 4,195,074 A * | 3/1980 | Safford, Jr. | ............ | A61K 39/20 435/239 |
| 5,910,573 A * | 6/1999 | Pluckthun | ............... | C07K 16/00 424/130.1 |
| 6,596,476 B1 * | 7/2003 | Lesniewski | .......... | C07K 14/005 435/5 |
| 8,039,588 B2 * | 10/2011 | Pancer | ............... | C07K 14/7051 530/350 |
| 8,394,771 B1 * | 3/2013 | Fang | .................. | C07K 14/4705 435/69.7 |
| 9,127,087 B2 * | 9/2015 | Pancer | ............... | C07K 14/7158 |
| 2005/0227297 A1 * | 10/2005 | D'Andrea | .............. | G01N 33/68 435/7.2 |
| 2011/0230374 A1 | 9/2011 | Pancer et al. | | |

FOREIGN PATENT DOCUMENTS

WO WO 2006/083275 A2 * 8/2006
WO 2010/065407 * 6/2010

OTHER PUBLICATIONS

Almogren et al., 2012. Ant-Thomsen-Friedenreich-Ag (anti-TF-Ag) potential for cancer therapy. Front. Biosci. S4: 840-863.*
Buonaguro et al., 2011. Translating tumor antigens into cancer vaccines. Clin. Vacc. Immunol. 18: 23-34.*
Clausen et al., 1989. ABH and related histo-blood group antigens; immunochemical differences in carrier isotypes and their distribution. Vox Sang. 56: 1-20.*
Fujitani et al., 2000. Distribution of H type 1-4 chains of the ABO(H) system in different types of human respiratory epithelium. J. Histochem. Cytochem. 48: 1649-1655.*
Ito et al., 1989. Histochemical demonstration of O-glycosidically linked, type 3 based ABH antigens in human pancreas using lectin staining and glycosidase digestion procedures. Histochemistry 92: 307-312.*
Martignone et al., 1989. Relationship between CaMBr1 expression and tumor progression in small lung carcinoma. Tumori 75: 373-377.*
Pollara et al., 1970. The evolution of the immune response. VII. Antibody to human "O" cells and properties of the immunoglobulin in lamprey. J. Immunol. 105: 738-745.*
Ravn et al., 2007. The Thomsen-Friedenreich disaccharide as antigen for in vivo tumor targeting with multivalent scFvs. Cancer Immunol. Immunother. 56: 1345-1347.*
Sylvestre et al., 2002. A collagen-like surface glycoprotein is a structural component of the Bacillus anthracis exosporium. Mol. Microbiol. 45: 169-178.*
Aldobati et al., 1997. In vitro mimicry of CaMBr1 tumor-associated antigen by synthetic oligosaccharides. Glycobiol. 7: 173-178.*
Binz et al., 2005. Engineering novel binding proteins from nonimmunoglobulin domains. Nature Biotechnology 23: 1257-1268.*
Clausen et al., 1986. Novel blood group H glycolipid antigens exclusively expressed in blood group A and AB erythrocytes (type 3 chain H). J. Biol. Chem. 261: 1380-1387.*

(Continued)

*Primary Examiner* — Christine Foster
(74) *Attorney, Agent, or Firm* — Wenderoth, Lind & Ponack, L.L.P.

(57) ABSTRACT

The invention relates to dimeric proteins comprised of subunits having (i) recombinant lamprey variable lymphocyte receptor (VLR) diversity regions linked to (ii) multimerization domains. The dimeric proteins exhibit binding specificity for glycosylated antigens, and they may be used in methods of detecting or isolating glycans from a sample, and in methods of disease diagnosis, prognosis, progression monitoring, treatment, and imaging.

15 Claims, 13 Drawing Sheets

(56) References Cited

OTHER PUBLICATIONS

Hey et al., 2005. Artificial, non-antibody binding proteins for pharmaceutical and industrial applications. Trends in Biotechnol. 23: 514-522.*

Le Pendu et al., 2011. ABH and Lewis histo-blood group antigens in cancer. APMIS 109: 9-31.*

Skerra, 2007. Alternative non-antibody scaffolds for molecular recognition. Curr. Opinion Biotechnol. 18: 295-304.*

Harlow, E. and Lane, D., Antibodies: A Laboratory Manual (1988) Cold Spring Harbor Laboratory Press, Cold Spring Harbor, NY, pp. 23-26.*

Lederman et al. "A single amino acid substitution in a common African allele of the CD4 molecule ablates binding of the monoclonal antibody, OKT4" Mol Immunol. Nov. 1991;28(11):1171-81.*

Colman et al. Research in Immunology, 1994; 145(1): 33-36.*

Brown et al. J Immunol. May 1996;156(9):3285-91.*

Tasumi, S. et al., High-affinity lamprey VLRA and VLRB monoclonal antibodies, PNAS, 2009, vol. 106, No. 31, pp. 12891-12896.

Herrin, B. et al., Structure and specificity of lamprey monoclonal antibodies, PNAS, 2008, vol. 105, No. 6, pp. 2040-2045.

Alder, M. et al., Antibody responses of variable lymphocyte receptors in the lamprey, Nature Immunology, 2008, vol. 9, No. 3, pp. 319-327.

Alder, M. et al., Diversity and function of adaptive immune receptors in a jawless vertebrate, Science, 2005, vol. 310, No. 5756, pp. 1970-1973.

Hong, X. et al., Sugar-binding proteins from fish: Selection of high affinity "lambodies" that recognize biomedically relevant glycans, ACS Chem. Biol., Oct. 8, 2012, pre-publication.

Hong, X. et al., Sugar-binding proteins from fish: Selection of high affinity "lambodies" that recognize biomedically relevant glycans, ACS Chem. Biol., Jan. 18, 2013; vol. 8, No. 1, pp. 152-160.

International Search Report for PCT/US2012/066413, dated Feb. 1, 2013.

Pancer, Z. et al. Somatic diversification of variable lymphocyte receptors in the agnathan sea lamprey. Nature, 2004, vol. 430, 174-180.

Han, B.W. et al. Antigen Recognition by Variable Lymphocyte Receptors. Science, 2008, 321(5897):1834-1837.

* cited by examiner

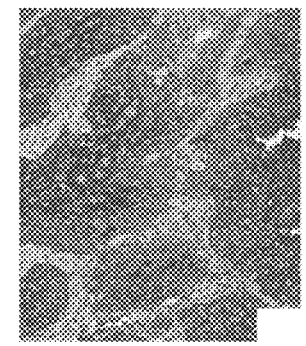
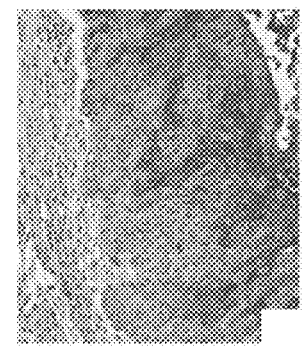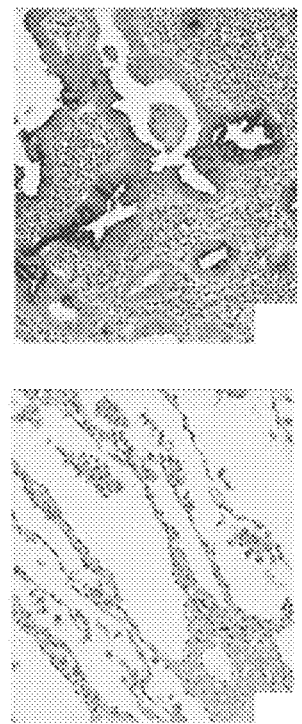
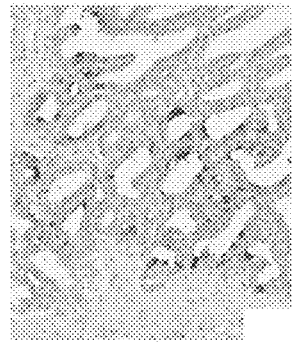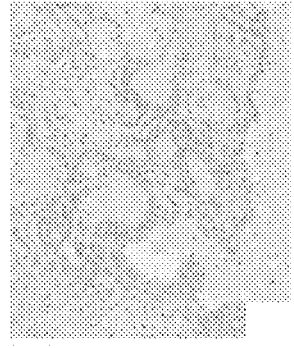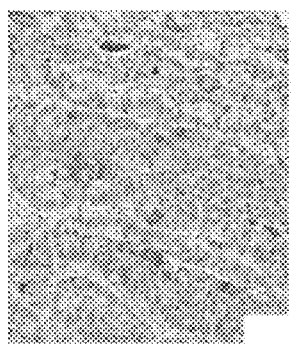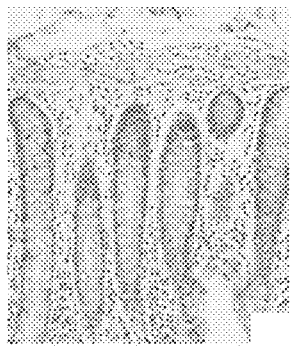

FIG. 8A
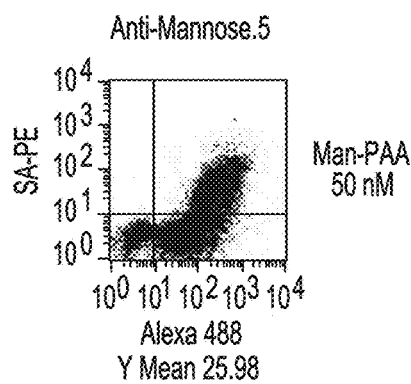
FIG. 8B
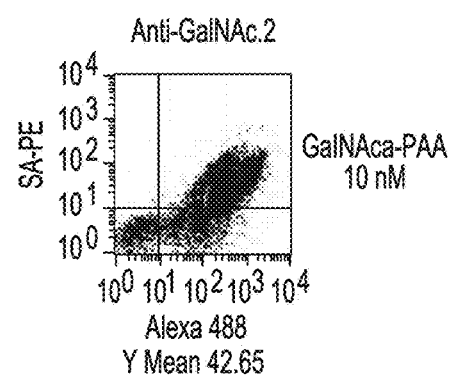
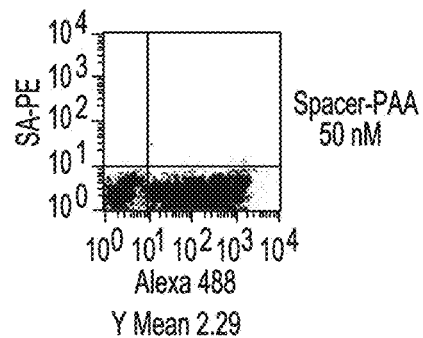
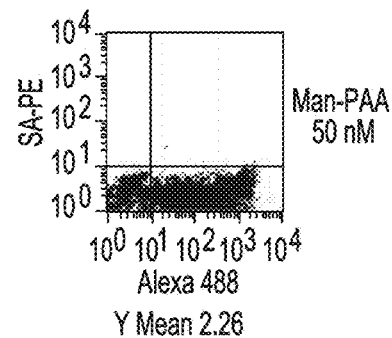

FIG. 8C
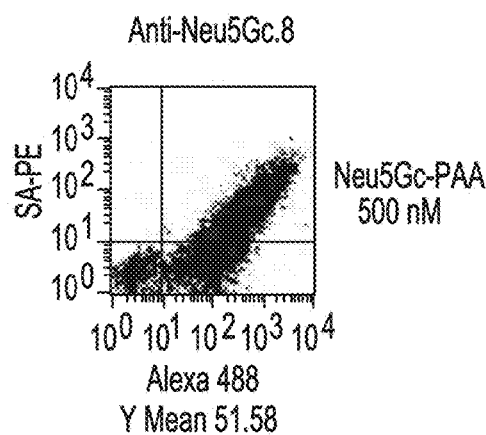
FIG. 8D
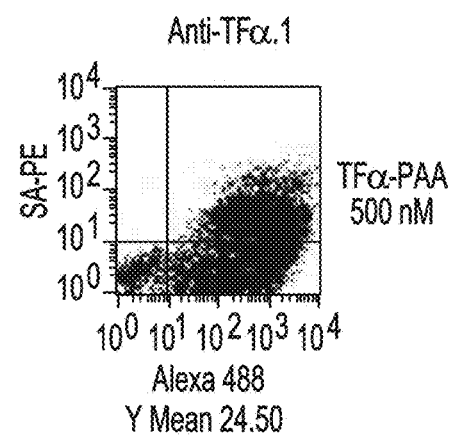
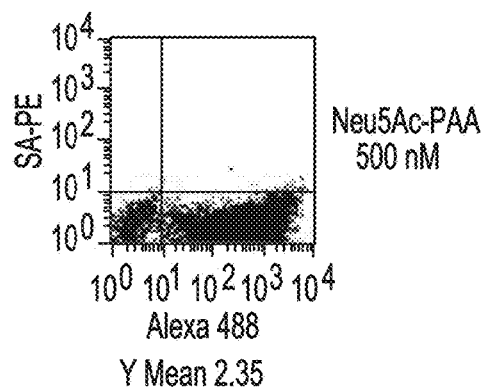
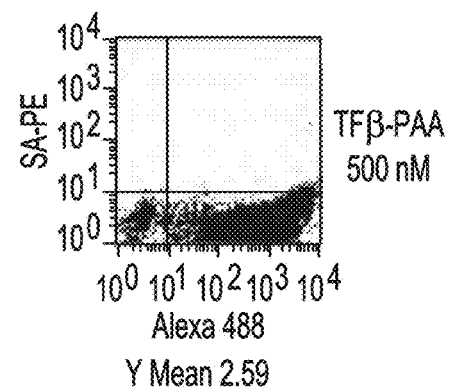

FIG. 8E
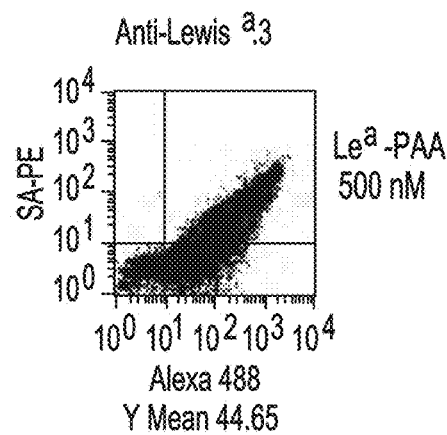
FIG. 8F
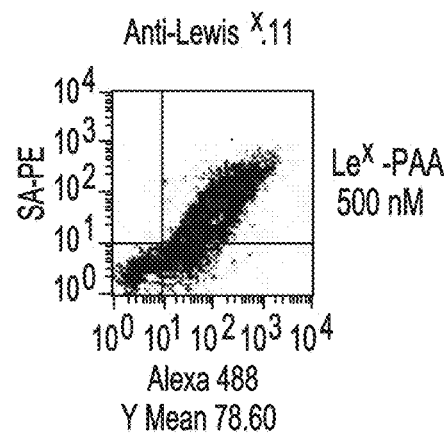
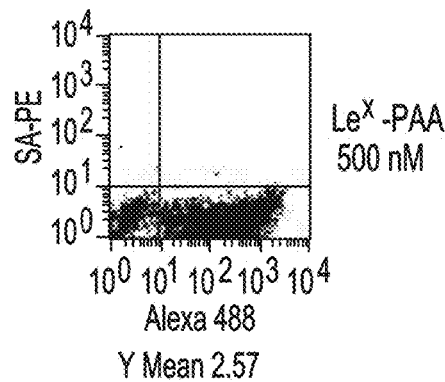
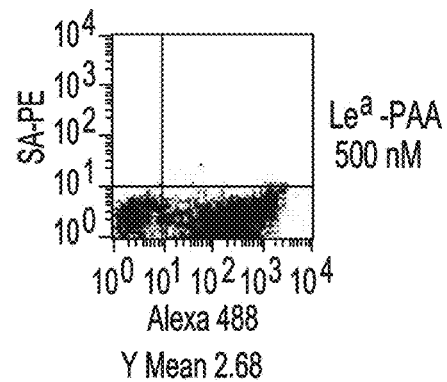

FIG. 8G
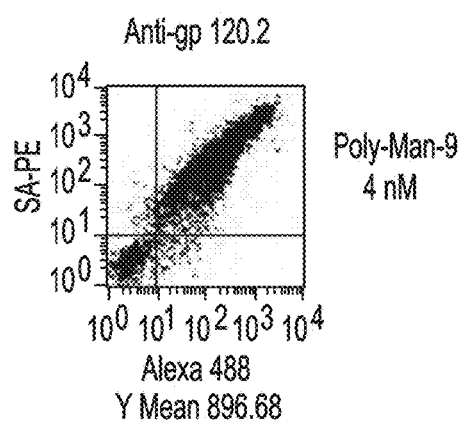
FIG. 8H
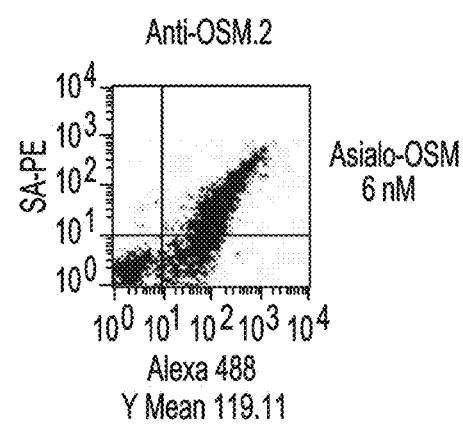
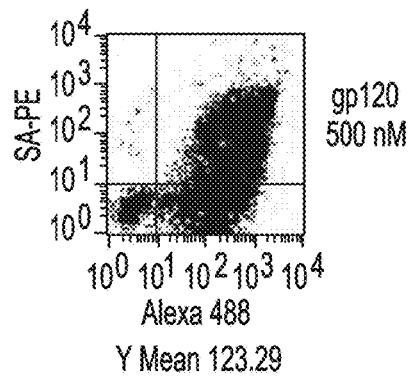
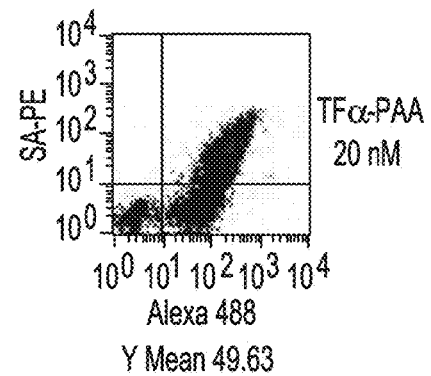

US 10,036,747 B2

LAMBODIES WITH HIGH AFFINITY AND SELECTIVITY FOR GLYCANS AND USES THEREFOR

STATEMENT OF FEDERALLY SPONSORED RESEARCH AND DEVELOPMENT

This invention was made with government support under Grant Number MCB0614672 awarded by the National Science Foundation. The government has certain rights in the invention.

TECHNICAL FIELD

The invention relates to dimeric proteins comprised of subunits having (i) recombinant lamprey variable lymphocyte receptor (VLR) diversity regions linked to (ii) multimerization domains. The dimeric proteins exhibit binding specificity for glycosylated antigens, and they may be used in methods of detecting or isolating glycans from a sample, and in methods of disease diagnosis, prognosis, progression monitoring, treatment, and imaging.

BACKGROUND OF INVENTION

Glycosylation of proteins is the most common and diverse form of post-translational modification. It can profoundly affect the function of glycoproteins in normal and pathological states, for example in cell-cell adhesion, fertilization, inflammation and malignant transformation (Varki et al., 2009). Most human tumor cells express glycoproteins with aberrant glycosylation patterns. The most studied cancer-specific glycans are truncated O-glycans such as the T-nouvelle antigen (Tn; GalNAcα) and the Thomsen-Friedenreich pancarcinoma tumor-associated carbohydrate antigen (TFα, Galβ1-3GalNAcαα1-Ser/Thr), which uniquely decorate mucin-type glycoproteins in about 90% of human cancer cells, but are distinctly absent from normal tissues except for the placenta in early pregnancy. The presence of such cancer-specific glycans can indicate increased invasiveness and metastatic potential.

Carbohydrate-binding proteins have therefore enormous utility as tools to monitor the expression of glycans for a wide range of basic research and clinical applications. For instance, a number of carbohydrate-binding lectins and mammalian antibodies have been used to detect expression of tumor-associated carbohydrate antigens for diagnostic and prognostic purposes (Powlesland et al., 2009; Li et al., 2010; Almogren et al., 2012). Glycan-binding proteins can also be used for a variety of in vivo applications, such as targeting specific cells and tissues for imaging, for drug delivery, and to control carbohydrate-mediated processes. Unfortunately, most readily available glycan-binding proteins, such as plant and animal lectins, and mammalian antibodies, typically display either broad reactivity, poor specificity, or both. For example, most monoclonal antibodies (mAb) that specifically recognize the Thomsen-Friedenreich antigen are of the IgM isotype, which are large antibodies with relatively low affinity, and therefore have limited clinical utility (Almogren et al., 2012). Furthermore, carbohydrate-binding proteins are only available for a tiny fraction of over 7,000 glycan determinants estimated for the human glycome (Cummings, 2009). Therefore, methods to generate tailored glycan-binding proteins with high affinity and selectivity for any glycan of interest could revolutionize the field.

A number of strategies have been evaluated for obtaining glycan-binding receptors. The most commonly used approach involves immunizing animals with an appropriate glycan or glycoconjugate to raise mAbs (Rittenhouse-Diakun et al., 1998; Li et al., 2010), but this process can be slow and labor intensive. This approach works well in certain cases, but many interesting glycans are conserved among species and, therefore, are non-immunogenic. Other approaches include directed evolution of lectins (Powlesland et al., 2009; Hu et al., 2012) and of single chain Fv antibodies (scFv) (Ravn et al., 2007; Sakai et al., 2010), small peptide carbohydrate receptors (Boltz et al., 2009) and carbohydrate-binding aptamers (Sun et al., 2010), but these have not proven to be general methods and have not gained widespread use. Therefore, a simple, efficient, and general method is still critically needed.

BRIEF SUMMARY OF INVENTION

The present invention describes members of a new class of dimeric glycan-binding proteins that exhibit binding specificity for glycosylated antigens. These dimeric proteins, termed lambodies, are comprised of two lambody subunits. Each subunit is a fusion protein comprising a diversity region from recombinant lamprey variable lymphocyte receptors (VLRs) linked to a multimerization domain that permits the lambody subunits to dimerize. The present invention also describes the use of lambodies in methods of detecting or isolating glycans from a sample, and in methods of disease diagnosis, prognosis, progression monitoring, treatment, and imaging.

In a first aspect, the invention is drawn to a lambody subunit, wherein the lambody subunit is a fusion protein comprising a lamprey VLR diversity region linked to a multimerization domain. The lambody subunits of the invention exhibit binding specificity for a glycan, glycolipid or glycoprotein. In some embodiments, the lambody subunits comprise a VLR diversity region selected from between the amino acid sequence of SEQ ID NO: 2 or 4.

In a second aspect, the invention is drawn to a lambody, wherein the lambody comprises two lambody subunits dimerized via their multimerization domains. The lambodies of the invention also exhibit binding specificity for a glycan, glycolipid or glycoprotein. In one embodiment of this aspect, the lambodies exhibit a binding affinity ($K_D$) for a target glycan, glycolipid or glycoprotein of at least about $1 \times 10^{-7}$ M. In some embodiments, the lambody subunits comprise VLR diversity regions having identical amino acid sequences. In some embodiments, the lambody subunits comprise VLR diversity regions having different amino acid sequences. In some embodiments, the lambody subunits comprise a VLR diversity region selected from between the amino acid sequence of SEQ ID NO: 2 or 4. In some embodiments, the both lambody subunits comprise an amino acid sequence set forth in SEQ ID NO:5, 6, 7 or 8.

In a third aspect, the invention is drawn to a lambody multimer, wherein the lambody multimer comprises three or more lambody subunits multimerized via their multimerization domains. The lambody multimers of the invention also exhibit binding specificity for a glycan, glycolipid or glycoprotein.

In embodiments of the first, second and third aspects, the glycan, glycolipid or glycoprotein is a one or more members selected from the group consisting of mannose, the Tn pancarcinoma antigen (GalNAcα), N-glycolylneuraminic acid (Neu5Gcα), hydroxylated N-acetylneuraminic acid (Neu5Ac), TFα, Lewis A [Galβ1-3(Fucα1-4)GlcNAcβ], Lewis X [Galβ1-4(Fucα1-3)GlcNAcβ], poly-Man-9, asialo-ovine submaxillary mucin (aOSM), blood group H type 3 trisaccharide (BG-H3), the Thomsen-Friedenreich pancarcinoma tumor-associated carbohydrate antigen (TFα), TFα-Serine, glycoprotein gp120 and poly-Man9 (mannose). In particular embodiments, the glycan, glycolipid or glycoprotein is one or more selected from among the following: BG-H3, TFα, TFα-Serine, glycoprotein gp120 and poly-Man9.

In a fourth aspect, the invention is drawn to a method for isolating a glycan-bearing element from a sample, said method comprising (i) adhering a lambody subunit, lambody or lambody multimer to a support, (ii) contacting the support with a sample under conditions permitting binding of a glycan-bearing element in the sample to the lambody subunit, lambody or lambody multimer, (iii) washing unbound sample from the support, (iv) eluting the glycan-bearing element from the support, and (v) collecting the glycan-bearing element. In one embodiment, the support is beads in a column.

In a fifth aspect, the invention is drawn to a method for detecting a glycan, glycolipid or glycoprotein in biological sample from a subject, said method comprising contacting a biological sample from a subject with a lambody subunit, lambody or lambody multimer and detecting binding of the lambody subunit, lambody or lambody multimer to a glycan, glycolipid or glycoprotein in the sample. In an embodiment of this aspect, the lambody subunit, lambody or lambody multimer is conjugated to a detectable label. In another embodiment of this aspect, the lambody subunit, lambody or lambody multimer is detected using a labeled secondary binding moiety that binds the lambody subunit, lambody or lambody multimer.

In a sixth aspect, the invention is drawn to a method for diagnosing cancer in a subject, said method comprising (a) contacting a biological sample from a subject with a lambody subunit, lambody or lambody multimer that binds a glycan, glycolipid or glycoprotein associated with cancer and (b) detecting binding of the lambody subunit, lambody or lambody multimer to the glycan, glycolipid or glycoprotein in the sample. In an embodiment of this aspect, the lambody subunit, lambody or lambody multimer is conjugated to a detectable label. In another embodiment of this aspect, the lambody subunit, lambody or lambody multimer is detected using a labeled secondary binding moiety that binds the lambody subunit, lambody or lambody multimer. In a further embodiment, the cancer is breast cancer, lung carcinoma, lung adenocarcinoma, large cell carcinoma, squamous cell carcinoma, prostate adenocarcinoma or colon adenocarcinoma.

In a seventh aspect, the invention is drawn to a method for making a prognosis of a subject having cancer, said method comprising (a) contacting a biological sample from a subject having cancer with a lambody subunit, lambody or lambody multimer that binds a glycan, glycolipid or glycoprotein associated with the cancer of the subject, (b) measuring the amount of lambody subunit, lambody or lambody multimer bound in (a), (c) comparing the amount measured in (b) with one or more amounts previously determined in control samples, and (d) making a prognosis of the subject based on the comparison in (c). In an embodiment of this aspect, the lambody subunit, lambody or lambody multimer is conjugated to a detectable label. In another embodiment of this aspect, the lambody subunit, lambody or lambody multimer is detected using a labeled secondary binding moiety that binds the lambody subunit, lambody or lambody multimer. In a further embodiment, the cancer is breast cancer, lung carcinoma, lung adenocarcinoma, large cell carcinoma, squamous cell carcinoma, prostate adenocarcinoma or colon adenocarcinoma.

In an eighth aspect, the invention is drawn to a method for monitoring progression of cancer in a subject, said method comprising (a) contacting a biological sample from a subject having cancer with a lambody subunit, lambody or lambody multimer that binds a glycan, glycolipid or glycoprotein associated with the cancer of the subject, (b) measuring the amount of lambody subunit, lambody or lambody multimer bound in (a), and (c) comparing the amount measured in (b) with one or more amounts previously determined in a biological sample from the subject. In an embodiment of this aspect, the lambody subunit, lambody or lambody multimer is conjugated to a detectable label. In another embodiment of this aspect, the lambody subunit, lambody or lambody multimer is detected using a labeled secondary binding moiety that binds the lambody subunit, lambody or lambody multimer. In a further embodiment, the cancer is breast cancer, lung carcinoma, lung adenocarcinoma, large cell carcinoma, squamous cell carcinoma, prostate adenocarcinoma or colon adenocarcinoma.

In a ninth aspect, the invention is drawn to a method for imaging cancer in a subject, said method comprising administering a labeled lambody subunit, lambody or lambody multimer to a subject and detecting the lambody subunit, lambody or lambody multimer in the subject, wherein the lambody subunit, lambody or lambody multimer binds a glycan, glycolipid or glycoprotein associated with cancer. In an embodiment, the cancer is breast cancer, lung carcinoma, lung adenocarcinoma, large cell carcinoma, squamous cell carcinoma, prostate adenocarcinoma or colon adenocarcinoma.

In a tenth aspect, the invention is drawn to a method for treating a subject having cancer, said method comprising administering a therapeutically-effective amount of a lambody subunit, lambody or lambody multimer to a subject having cancer, wherein the lambody subunit, lambody or lambody multimer binds a glycan, glycolipid or glycoprotein associated with the cancer of the subject. In an embodiment, the lambody subunit, lambody or lambody multimer is conjugated to a therapeutic agent, such as a chemotherapeutic agent. In a further embodiment, the cancer is breast cancer, lung carcinoma, lung adenocarcinoma, large cell carcinoma, squamous cell carcinoma, prostate adenocarcinoma or colon adenocarcinoma.

In relevant aspects of the invention, the biological sample is one or more selected from the group consisting of a bodily fluid, secretion or excretion, cells, tissue, or tissue biopsy. In relevant aspects of the invention, the biological sample may also be one or more selected from the group consisting of whole blood, plasma, serum, mucus, cerebrospinal fluid, pleural fluid, urine, tears, saliva, sputum, and stool.

In the method aspects of the invention, the lambody may be a lambody composed of pairs of one of the following lambody subunits: VLRB.aGPA.23-AGmFc (SEQ ID NO:5), VLRB.aGPA.23-GCN4 (SEQ ID NO:6), VLRB.gp120.4-AGmFc (SEQ ID NO:7), or VLRB.gp120.4-GCN4 (SEQ ID NO:8). Alternatively, the lambody may be composed of pairs of variants of these lambody subunits as defined herein for variants of the lambody subunits. In further additional aspects, each of the methods of the invention may be practiced using a lambody subunit, lambody or lambody multimer that has binding specificity to a glycan, glycolipid or glycoprotein displayed by a cancer but either not displayed or displayed at a reduced level in counterpart normal cells or tissue. Thus, the methods of the present invention can be practiced using lambody subunits, lambodies or lambody multimers not specifically disclosed herein.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 4A-4H. Lambody staining of human normal and cancer tissues. (FIG. 4A) Normal lung (tumor adjacent). (FIG. 4B) Large cell carcinoma. (FIG. 4C & FIG. 4D) Squamous cell carcinoma. (FIG. 4E) Normal colon (tumor adjacent). (FIG. 4F) Colon adenocarcinoma. (FIG. 4G) Normal prostate. (FIG. 4H) Prostate adenocarcinoma. Images were scanned at 20× magnification. Tissue microarray slides were incubated with 5 µg/mL of VLRB.aGPA.23-mFc overnight at 4° C., and immune complexes were detected with anti-mouse IgG-HRP and DAB substrate (brown), then counterstained with Hematoxylin (blue).

(FIG. 5A) Summary of staining lung tumors and adjacent normal lung tissues (n=112). Samples were ranked based on image analysis scores for fractions of positively staining cells per tissue core. Positive staining—merged medium and high intensity scores per tissue; Negative staining—merged unstained and low intensity scores per tissue. Cases of non-small cell lung cancers (NSCLC; n=88) are shaded grey. (FIG. 5B) Relationship between overall survival rate of NSCLC patients, and staining with VLRB.aGPA.23. Kaplan-Meier curve for samples that stained positive (n=24; lighter grey, lower line), compared to negative staining (n=64; darker grey, upper line). Inset: p value calculated using the Mantel-Cox log-rank chi-squared test.

FIGS. 8A-8H. Survey of VLR clones that can selectively bind monosaccharides, disaccharides, trisaccharides, polysaccharides and glycoproteins. Dot-plot presentation of labeling intensities, and measurement of the Y-mean fluorescence intensities from ligand binding for a representative clone from each screen. (FIG. 8A) Anti-Mannose.5 labeled with the indicated concentrations of Mannose-PAA and the control spacer-PAA (Y-mean<3 indicates no binding). (FIG. 8B) Anti-GalNAc.2 labeled with GalNAcα-PAA and Man-PAA. (FIG. 8C) Anti-Neu5Gc.8 labeled with Neu5Gcα-PAA and Neu5Acα-PAA. (FIG. 8D) Anti-TFα. 1 labeled with TFα-PAA and TFβ-PAA. (FIG. 8E) Anti-Lewis$^a$.3 labeled with Lewis$^a$-PAA and Lewis$^x$-PAA. (FIG. 8F) Anti-Lewis$^x$. 11 labeled with Lewis$^x$-PAA and Lewis$^a$-PAA. (FIG. 8G) Anti-gp120.2 labeled with poly-Man9-PAA and gp120. (FIG. 8H) Anti-OSM.2 labeled with aOSM and TFα-PAA. Biotinylated antigens were detected with SA-PE, and the level of VLR surface display was detected by labeling with rat anti-FLAG mAb followed by anti-rat Alexa 488 antibodies.

DETAILED DESCRIPTION OF THE INVENTION

Definitions

Figure 1:
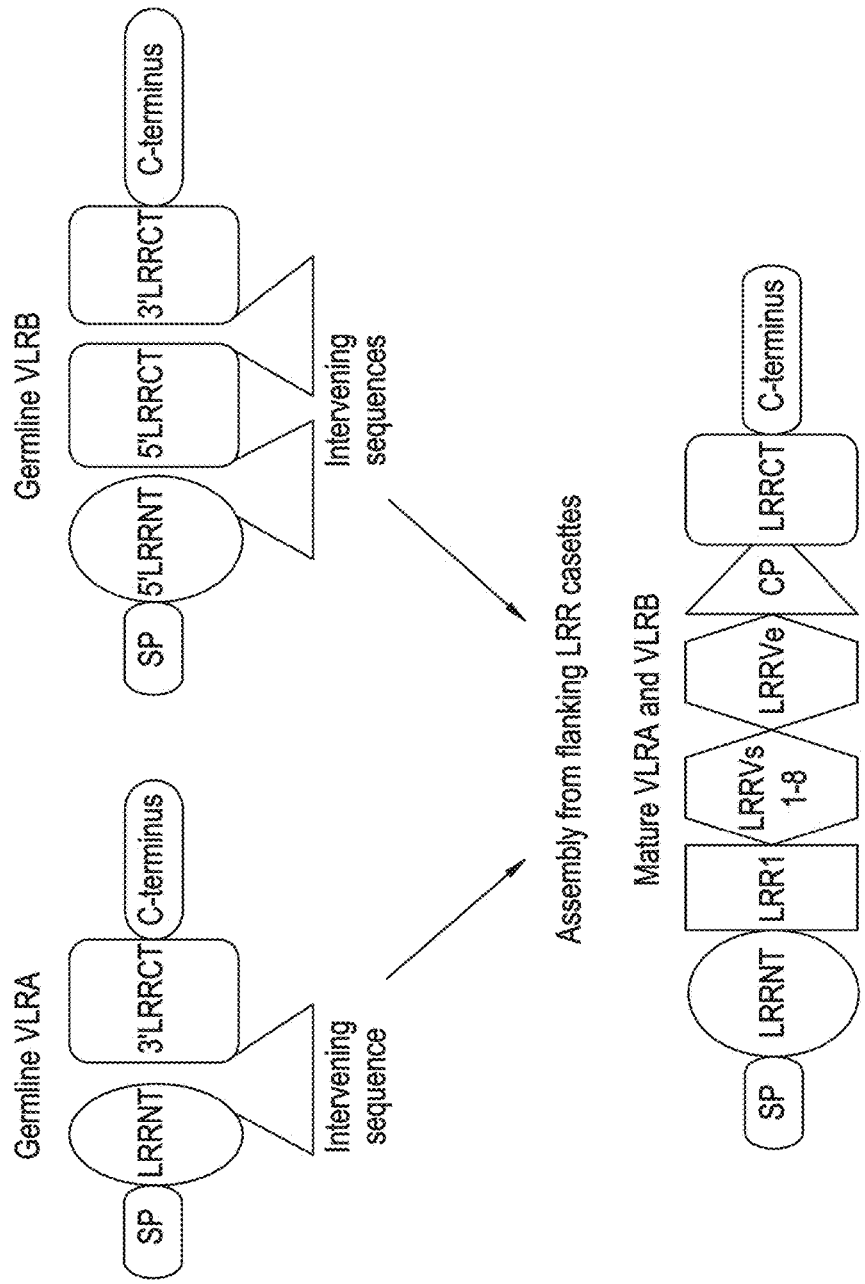
FIG. 1. Assembly of lamprey germline VLR genes into mature VLRs. The germline genes are nonfunctional, consisting only of the invariant portions: N-terminal signal peptide (SP), a complete or 3'-truncated portion of the LRRNT, 1 or 2 noncoding intervening sequences, 1 or 2 truncated portions of the LRRCT, and a stalk-like C terminus that includes a glycosyl phosphatidylinositol (GPI) membrane anchorage motif, which tethers the VLR to the lymphocyte surface. The diversity regions of mature VLR genes consist of LRRNT of 27-34 residues, one 25-residue LRR (LRR1), up to nine 24-residue LRRs (LRRVs, the terminal one designated LRRVe), one 16-residue truncated LRR designated CP, and 48-63 residue LRRCT. The mature VLR genes are assembled by sequential insertion of LRR-encoding cassettes, from arrays of the hundreds of cassettes flanking each gene (not shown), into the incomplete germline genes via a gene conversion-like process. The germline VLR gene portions of LRRNT and LRRCT serve as docking sites for the incoming LRR cassettes.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the terms "treating" and "treatment" have their ordinary and customary meanings, and include one or more of: ameliorating a symptom of disease; blocking or ameliorating a recurrence of a symptom of disease; decreasing in severity and/or frequency a symptom of disease; slowing, interrupting, arresting, controlling, or stopping the progression of the disease. The terms do not necessarily indicate a total elimination of the disease or a symptom of the disease. Treatment means ameliorating, blocking, reducing, decreasing or inhibiting by about 1% to about 100% versus a subject to which the lambodies have not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which the lambodies have not been administered.

The Invention

Variable lymphocyte receptors (VLRs) are the antibodies of jawless fish such as lamprey and hagfish. VLRs are assembled in lymphocytes by DNA rearrangements and they are as diverse as the conventional antibodies of jawed vertebrates from shark to man, with a potential repertoire of over $10^{14}$ unique receptors. However, VLRs are uniquely built from highly diverse leucine-rich repeat modules, instead of the immunoglobulin building blocks of conventional antibodies (Pancer et al., 2004; Alder et al., 2005; Tasumi et al., 2009).

There are 2 types of VLR genes (Pancer et al., 2005; Rogozin et al., 2007), VLRA and VLRB, expressed by mutually exclusive lymphocyte populations (Alder et al. 2008). To form mature functional receptors, germline VLR genes undergo DNA recombination, whereby each VLR is assembled from multiple leucine-rich repeat (LRR)-encoding modules selected from arrays of several hundred cassettes flanking each VLR gene. Mature VLRs consist of N-terminal leaders and C-terminal stalk-like cell surface-anchoring domains encoded by the germline VLR genes. Each VLR has a unique diversity region. Only small amino- and carboxy-terminal portions of the diversity regions are contributed by the germline genes (FIG. 1); these serve as docking sites for the sequential incorporation of LRR cassettes via a gene conversion-like process (Rogozin et al., 2007; Nagawa et al. 2007).

The diversity regions in VLRA and VLRB consist of sets of LRR modules, each with a highly variable sequence: a 27- to 34-residue N-terminal LRR (LRRNT), one 25-residue LRR (LRR1), up to nine 24-residue LRRs (LRRVs; the terminal one designated LRRVe), one 16-residue truncated LRR designated the connecting peptide (CP), and a 48- to 63-residue C-terminal LRR (LRRCT) (see also FIG. 1). The LRRNT and LRRCT are stabilized by 2 sets of intramodular disulfide bonds that serve to cap both ends of the curved, solenoid-shaped diversity region (Kim et al. 2007). The assembly of VLRs by iterated cassette insertions, with frequent recombination events within boundaries of the LRR modules, generates a vast repertoire of receptors estimated at more than $10^{14}$ unique VLRs, of comparable magnitude to mammalian antibodies and TCRs (Adler et al. 2005; Rogozin et al., 2007).

A technology for production and high-throughput screening of recombinant antigen-binding VLR diversity regions, from libraries of over $10^8$ independent clones, has been developed using a unique VLR diversity region yeast surface display platform (see U.S. Patent Publication No. 20110230374, herein incorporated by reference in its entirety; see also Tasumi et al., 2009). These libraries are screened for clones that can selectively bind glycans, glycolipids and glycoproteins. This technology thus permits the production and screening of single-chain, monoclonal lamprey VLR diversity regions that exhibit high affinity against nearly all tested proteins, glycoproteins, glycolipids and glycan antigens. Two VLR diversity regions identified in screens are VLRB.aGPA.23 and VLRB.gp120.4. VLRB.aGPA.23 has the amino acid sequence set forth in SEQ ID NO:2. This VLR diversity region has binding specificity for BG-H3, TFα and TFα-Serine glycans. The nucleotide sequence encoding this diversity region is provided in SEQ ID NO: 1, which is also encompassed within the scope of the invention. Thus, the invention includes diversity region VLRB.aGPA.23, comprising or consisting of the amino acid sequence set forth in SEQ ID NO:2. VLRB.gp120.4 has the amino acid sequence set forth in SEQ ID NO:4. This diversity region has binding specificity for glycoprotein gp120 and poly-Man9 (mannose). The nucleotide sequence encoding this diversity region is provided in SEQ ID NO:3, which is also encompassed within the scope of the invention. Thus, the invention includes diversity region VLRB.gp120.4, comprising or consisting of the amino acid sequence set forth in SEQ ID NO:4.

On the surface of yeast, monomeric VLRs are displayed at densities that can enable cooperative binding by several VLRs of multivalent antigens, such as most glycoconjugates, generating stable complexes due to the high avidity (Tasumi et al., 2009, Hong et al., 2012).While the lamprey VLR diversity regions exhibit moderate (micromolar) affinity binding to glycoproteins, glycolipids and glycan antigens, the inventors have now discovered, as described herein, that when at least two of the diversity regions are linked together, the binding affinities can be greatly increased, sometimes on the order of 1000-fold or greater (low nanomolar to picomolar). The present application is therefore addressed, in part, to dimeric proteins comprising two lamprey VLR diversity regions.

In particular, the present invention is directed, in part, to dimeric glycan-binding proteins that exhibit binding specificity for glycosylated antigens. These dimeric proteins, termed lambodies, are comprised of two lambody subunits. Each subunit is a fusion protein comprising a diversity region from recombinant VLRs linked to a multimerization domain that permits the lambody subunits to dimerize. The present invention is also directed to particular lambodies, prepared from lamprey VLR diversity regions identified in screens of the library referenced herein using selected glycans, glycolipids and glycoproteins. The present invention is further directed to the lambody subunits, as well as variants thereof that have one or more amino acid changes in the VLR diversity region when compared to the lambody subunit upon which they are based. The present invention is also further directed to lambodies multimers comprising three or more lambody subunits. As discussed in more detail below, some of the lambodies of the invention bind with specificity to antigens in a variety of tumors, with little or no binding in normal tissues or in tumor-adjacent benign tissue.

As used herein, the terms "lambody" and "lambodies" are often used, for the sake of brevity, to generically refer to all forms and types of lambodies described herein, including lambody subunits, variants of the lambody subunits, lambodies, and lambody multimers. Therefore, unless the context indicates otherwise, reference herein to "lambody" or "lambodies" includes one or more lambody subunits, variants of lambody subunits, lambodies, and lambody multimers.

The lambodies of the present invention have many advantages over conventional antibodies, e.g., antibodies produced by the workhorses of immunology including mice and rabbits and humans. Some of these advantages are illustrated in Table 1.

TABLE 1

Biochemical and biophysical properties of mammalian antibodies and lambodies.

| | Conventional antibodies | Lambodies |
|---|---|---|
| Diversity | Over $10^{14}$ combinations | Over $10^{14}$ combinations |
| Affinity | High, antigen binding interface: 1,400-2,300 Å$^2$ | High, antigen binding interface: 1,700-1,800 Å$^2$ |
| Structure and size | Heterotetramer, 150 kDa | Homodimer: 60-105 kDa |
| Stability | Moderate | Highly resistant to pH, temperature, denaturants |
| Glycosylation | N-glycan | None |
| Recognition of glycans | Poor | Excellent |

The lambodies can be used to specifically bind a glycan, glycolipid or glycoprotein, e.g. to isolate or purify a glycan, glycolipid or glycoprotein from a more complex mixture; to detect a disease-associated glycan, glycolipid or glycoprotein for diagnosis, prognosis, progression monitoring or imaging of the disease as described above; and to target a treatment to a diseased tissue in which the disease-associated glycan, glycolipid or glycoprotein is produced, to name a few uses.

In a particular aspect, the lambodies of the invention can be used for cancer diagnosis, prognosis, progression monitoring, treatment, and imaging. For example, lambodies can be used to detect and/or measure tumor glycans in bodily fluids, secretions, or excretions, e.g., blood, serum, mucus, urine, tears, saliva, sputum, stool, and the like, for initial cancer diagnosis and/or prognosis, which will provide better preclinical assessment at stages when medical intervention is most efficient. Lambodies can be used to monitor tumor recurrence, burden or progression. Lambodies can further be used to monitor therapeutic efficacy. Lambodies also can be used to detect/measure tumor glycans in cell or tissue biopsies for diagnosis and/or prognosis. Lambodies can be coupled to imaging agents to allow tumor imaging, e.g., for initial diagnosis/prognosis, to monitor recurrence, and/or to monitor therapeutic efficacy.

Considering the biological roles of glycoproteins and their glycan structures in tumor cell invasion and metastasis, and the extraordinary high binding affinities of some of the types of lambodies, the lambodies can be used to interfere with functions of the glycoprotein-carriers of tumor-associated carbohydrate structures, and act as tumor targeting therapeutic agents that can save many human lives. Lambodies can therefore be used for tumor immunotherapy, for example, alone, in conjunction with other cancer treatments, as fusion proteins or conjugated to radionuclides, toxins, or other chemotherapeutic agents.

Lambody Subunits

The present invention is generally directed, in one aspect, to lambody subunits. As suggested above, the lambody subunits of the present invention are fusion proteins comprising a lamprey VLR diversity region linked to a multimerization domain. The lambody subunits of the present invention further exhibit binding specificity for a glycan, glycolipid or glycoprotein.

As discussed above, a lamprey VLR diversity region is that portion of a lamprey VLR that comprises, in 5' to 3' order, one 27- to 34-residue N-terminal LRR (LRRNT), one 25-residue LRR (LRR1), up to nine 24-residue LRRs (LRRVs; the terminal one designated LRRVe), one 16-residue truncated LRR (CP), and a 48- to 63-residue C-terminal LRR (LRRCT). Reference can be made to FIG. 1 which provides the ordering of the different modules. The lamprey VLR diversity regions used in the lambodies of the present invention may be naturally-occurring lamprey VLR diversity regions, whether isolated directly from a lamprey or isolated from a library (e.g., SEQ ID NOs:2 and 4), such as the yeast display library described herein and in Tasumi et al. (2009). The lamprey VLR diversity regions may also be chemically produced, such as where a specific amino acid sequence is desired; or a combination thereof may be used, such as where selected changes are made to a naturally-occurring lamprey VLR diversity region (e.g., by affinity maturation as will be understood by the skilled artisan). The invention encompasses lamprey VLR diversity regions having 1, 2, 3, 4, 5, 6, 7, 8 or 9 of the 24-residue LRRVs.

The dimerization domains that are used in the lambody subunit fusion proteins may be any that permit two VLR diversity regions to form a dimeric protein. Such domains include, but are not limited to, a portion of an antibody, e.g., the Fc portion of an IgG antibody, a leucine zipper dimerization domain from the yeast GCN4 protein (e.g., RMK- QLEDKVEELLSKNYHLENEVARLKKLVGER (SEQ ID NO:9); see also Stefan et al., 2011) or other leucine zipper dimerization domains, a combination that includes a partial hinge region of an antibody and the leucine zipper dimerization domain from yeast (see, e.g., FIG. 9, and SEQ ID NOs: 6 and 8), and coil-coiled dimerization peptides. Acceptable domains also include those that permit formation of a disulfide bridge between the two domains. The disulfide bridge may be formed between cysteine residues that are naturally-occurring in the domain, or between cysteine residues added to the amino- or carboxy-terminus of the domain, or within the domain.

The portion of an antibody to which the lamprey VLR diversity region can be linked may be any portion of any type (e.g., IgG, IgE, IgM, IgD, IgA and IgY), class (e.g., IgG1, IgG2, IgG3, IgG4, IgA1 and IgA2) or subclass of immunoglobulin molecule as long as it has the ability to multimerize. Exemplary portions of antibodies include Fc fragments (an antibody fragment that contains the hinge region and constant regions); Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')$_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes); a single-chain Fv (scFv) comprising the VH and VL domains of an antibody, wherein these domains are present in a single polypeptide chain; and derivatives of antibodies that include one or more CDR sequences of an antibody combining site (the CDR sequences may be linked together on a scaffold when two or more CDR sequences are present). Where a portion of an antibody is used as the multimerization domain, such as the Fc portion of an IgG antibody, the peptide may be used with its natural complement of sugars, or it may be used in an aglycosylated form (Sazinsky et al., 2008).

The lambody subunits of the present invention will commonly have the lamprey VLR diversity region on the amino terminal end of the protein, and the multimerization domain at the carboxy terminus, although in some embodiments, the order may be reversed.

Lambody subunits encompassed within the scope of the invention include lambody subunits with binding specificity for glycoconjugates and glycoproteins that display important biomedical glycotopes. These glycans, glycolipids and glycoproteins include monosaccharides such as mannose, the Tn pancarcinoma antigen (GalNAcα), N-glycolyl-neuraminic acid (Neu5Gcα), and a dietary-derived hydroxylated form of N-acetylneuraminic acid (Neu5Ac) that can cause chronic inflammation and carcinomas. Also included are disaccharides, such TFα and TFα-Serine, and trisaccharides, such as Lewis A [Galβ1-3(Fucα1-4)GlcNAcβ] and Lewis X [Galβ1-4(Fucα1-3)GlcNAcβ], whose uniquely sialylated forms are characteristic of most cancer cells (Kannagi, 2007). Polysaccharides are also included, such as lambody subunits with binding specificity for poly-Man9 (mannose), and for glycoprotein gp120, a unique glycan of the HIV viral envelope (Wyatt et al., 1998). Lambody subunits of the present invention also include those having binding specificity to asialo-ovine submaxillary mucin (aOSM), whose native form consists of 50% carbohydrates, mostly sialyl-Tn (94%) and TFα (4%), and to blood group H type 3 trisaccharide (BG-H3, Fucα1-2Galβ1-3GalNAcα). In particular embodiments, the glycan, glycolipid or glycoprotein is one or more selected from among the following: BG-H3, TFα, TFα-Serine, glycoprotein gp120 and poly-Man9 (mannose).

Particular lambody subunits of the present invention include the following lambody subunits: VLRB.aGPA.23-AGmFc (SEQ ID NO:5), VLRB.aGPA.23-GCN4 (SEQ ID NO:6), VLRB.gp120.4-AGmFc (SEQ ID NO:7), and VLRB.gp120.4-GCN4 (SEQ ID NO:8). The VLRB.aGPA.23-based lambody subunits have binding specificity for BG-H3, TFα and TFα-Serine glycans. The VLRB.gp120.4-based lambody subunits have binding specificity for glycoprotein gp120 and poly-Man9 (mannose).

The lambody subunits of the present invention include variants having one or more amino acid changes, including substitutions, insertions and/or deletions, in a specific VLR diversity region. The variants have at least about 85% amino acid sequence identity with a VLR diversity region disclosed herein over the entire amino acid sequence of the diversity region. Variants also include those having at least about 86%, 87%, 88%, 89%, 90%, 91%, 92%, 93%, 94%, 95%, 96%, 97%, 98% or 99% sequence identity with a VLR diversity region disclosed herein. As an example, variants include those having sequence identity, such as at least about 90% sequence identity, with VLR diversity region VLRB.aGPA.23 (SEQ ID NO:2). In one embodiment, the variant comprises a VLR diversity region having the amino acid sequence set forth in SEQ ID NO:2 with one, two, three, four or all five of the amino acid mutations: S19N, S86G, H105R, K112M and T208S. As another example, variants of the lambody subunits include those having sequence identity, such as at least about 90% sequence identity, with the VLR diversity region of VLRB.gp120.4 (SEQ ID NOL:4).

The binding affinity with which the lambody subunits of the present invention bind to a glycan, glycolipid or glycoprotein is a $K_D$ value of at least about $1\times10^{-6}$ M, at least about $5\times10^{-6}$ M, at least about $1\times10^{-7}$ M, at least about $5\times10^{-7}$ M, at least about $1\times10^{-8}$ M, or at least about $5\times10^{-8}$ M.

Lambodies

The present invention also encompasses lambodies. Lambodies are similar to convention antibodies in that they contain two glycan binding sites on one dimeric molecule. Thus, lambodies are comprised of two lambody subunits where the multimerization domains have dimerized. Dimerization of the subunits may be induced using means appropriate for the multimerization domains used in the production of the subunits, including solutions comprising particular salts, buffers and/or pH.

The lambodies include homo-dimers, where the lamprey VLR diversity regions of the molecule are the same. An example is a lambody comprising two identical lamprey VLR diversity regions, each of which is linked to a leucine zipper dimerization domain, and where the multimerization domains are dimerized. Such molecules exhibit increased affinity for the glycan, glycolipid or glycoprotein by binding to two sites on the same molecule displaying the glycan, glycolipid or glycoprotein. The lambodies also include hetero-dimers where the subunits comprise VLR diversity regions that bind to different glycans. Such lambodies may exhibit increased affinity for the molecule displaying the glycan, glycolipid or glycoprotein by binding to different sugars on the same target molecule.

The binding affinity with which the lambodies of the present invention bind to a glycan, glycolipid or glycoprotein is a $K_D$ value of at least about $1\times10^{-7}$ M, at least about $5\times10^{-7}$ M, at least about $1\times10^{-8}$ M, at least about $5\times10^{-8}$ M, at least about $1\times10^{-9}$ M, at least about $5\times10^{-9}$ M, at least about $1\times10^{-10}$ M, at least about $5\times10^{-10}$ M, at least about $1\times10^{-11}$ M, at least about $5\times10^{-11}$ M, at least about $1\times10^{-12}$ M, or at least about $5\times10^{-12}$ M.

Lambody Multimers

The present invention also encompasses lambody multimers. Lambody multimers are similar to lambodies but they comprise three or more lambody subunits. The lambody multimers include lambody trimers, and lambody multimers having four, five, six, or more glycan binding sites. Multimerization of the subunits may be induced using means appropriate for the multimerization domains used in the production of the subunits, including solutions comprising particular salts, buffers and/or pH.

The lambody multimers include homo-multimers, where the lamprey VLR diversity regions of the molecule are the same. The lambody multimers also include hetero-multimers where the lambody subunits that comprise the multimers bind to different glycans.

Detectable Labels and Therapeutic Agents

The lambodies of the present invention can be conjugated to one or more molecules, where the molecules can serve diverse purposes including, but not limited to, detectable labels (e.g., for use in diagnosis and imaging) and therapeutic agents (e.g., for use in treatment). The skilled artisan will understand that many of the vast array of molecules that can be conjugated to conventional antibodies may be conjugated to the lambodies of the present invention. For example, lambodies can be conjugated to detectable labels such as an enzyme (e.g., peroxidase, alkaline phosphatase, glucose oxidase), a metal (e.g., gold for electron microscopy applications), a fluorescent marker (e.g., for immunofluorescence and flow cytometry applications, including CYE dyes, fluorescein isothiocyanate, rhodamine, phycoerytherin, phycocyanin, allophycocyanin, o-phthaldehyde and fluorescamine), a fluorescence-emitting metals (e.g., $^{152}$Eu), a radioactive marker (e.g., radioisotopes for diagnostic purposes, including $^3$H, $^{131}$I, $^{35}$S, $^{14}$C, and $^{125}$I), a chemiluminescent marker (e.g., luminol, luciferin, isoluminol, theromatic acridinium ester, imidazole, acridinium salt and oxalate ester), and a protein tag (e.g., biotin, phycobiliprotein, c-Myc, HA, VSV-G, HSV, FLAG, V5, or HIS). A specific example includes VLRB.aGPA.23-GCN4-biotin and VLRB.2D-GCN4-biotin (discussed in the Examples below). The labeled lambodies can be biotinylated via Maleimide-PEG$_2$-Biotin, yielding about 2 moles biotin per mole protein. The lambodies can be easily detected when used in the methods of the present invention.

The lambodies of the invention can also conjugated to therapeutic agents such as chemotherapeutic agents and radioimmunotherapeutic (RIT) agents. Suitable chemotherapeutic agents include, but are not limited to, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives. More particularly, chemotherapeutic agents may include amifostine (ethyol), cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

Methods

The present invention is also directed to the use of lambodies in a number of methods, including, but not limited to, methods for isolating glycan-bearing elements from a sample, methods for detecting glycans in a sample, and methods for the diagnosis, prognosis, progression monitoring, treatment, and imaging of diseases or conditions, such as cancer, in a subject. Each of the methods described herein can be performed using any lambody subunit, lambody, or lambody multimer that has binding specificity for a glycan, glycoprotein, or glycolipid, including the specific lambody subunits disclosed herein (e.g., VLRB.aGPA.23-AGmFc (SEQ ID NO:5), VLRB.aGPA.23-GCN4 (SEQ ID NO:6), VLRB.gp120.4-AGmFc (SEQ ID NO:7), and VLRB.gp120.4-GCN4 (SEQ ID NO:8)).

The methods of the present invention include methods for isolating a glycan-bearing element from a sample. Such methods comprise (i) adhering a lambody subunit, lambody or lambody multimer to a support, (ii) contacting the support with a sample under conditions permitting binding of a glycan-bearing element in the sample to the lambody subunit, lambody or lambody multimer, (iii) washing unbound sample from the support, (iv) eluting the glycan-bearing element from the support, and (v) collecting the glycan-bearing element. Due to the binding specificity exhibited by the lambodies of the invention, these molecules can be particularly useful in isolating glycan-bearing elements from a sample. While the methods need not be limited in their scope, an example of a useful manner in which the methods may be practiced is where one wishes to isolate a cell bearing a glycan-containing group from a biological fluid or where one wishes to isolate a glycan-bearing virus from a media in which the virus has been produced. The lambodies can be linked to a resin and formed into columns, for example, and the samples can be applied to the column, allowed to drain through, followed by washing of the column, and then elution of the glycan-bearing target from the column. The skilled artisan will understand that these methods need not be limited in scope. The glycan-bearing element or target can be any item bearing a glycan including, but not limited to, a protein, a carbohydrate, a cell, a group of cells, and an organism, such as a bacteria, virus and prion. The sample can be any material that contains the glycan-bearing element, including, but not limited to, a biological sample as defined herein, a culture media, cell lysate, a solution, such as a buffered solution, etc. As will be clear from the description above, in one embodiment, the lambodies are linked to a support, such as a chip, microarray or glass surface, or a filter, granular substance, resin or matrix for use in a column, such as beads or a matrix comprising agarose, glass, cellulose, or polyacrylimide, to name a few examples.

The methods of the present invention also include methods for detecting a glycan, glycolipid or glycoprotein in a sample. Such methods comprise contacting a sample with a lambody subunit, lambody or lambody multimer and detecting binding of the lambody subunit, lambody or lambody multimer to a glycan, glycolipid or glycoprotein in the sample. These methods can be used as a means for quickly determining whether a particular glycan, glycolipid or glycoprotein is in a sample, regardless of the source of the sample. Due to the fact that many glycans, glycolipids and glycoproteins are displayed on the surface of diseased cells, but not normal counterparts, this detection method is especially well-suited to biological samples. Therefore, the methods of the present invention also include methods for detecting a glycan, glycolipid or glycoprotein in biological sample from a subject. The methods comprise contacting a biological sample from a subject with a lambody subunit, lambody or lambody multimer and detecting binding of the lambody subunit, lambody or lambody multimer to a glycan, glycolipid or glycoprotein in the sample. Suitable means for detecting the lambody subunits, lambody and lambody multimers are discussed below, as are relevant biological samples.

The methods of the present invention further include methods for diagnosing a disease in a subject. Such methods comprise contacting a biological sample from a subject with a lambody subunit, lambody or lambody multimer that binds a glycan, glycolipid or glycoprotein associated with a disease and detecting binding of the lambody subunit, lambody or lambody multimer to the glycan, glycolipid or glycoprotein in the sample. In this manner, the disease can be diagnosed in the subject. Because many glycans, glycolipids and glycoproteins are displayed on the surface of diseased cells, but not normal counterparts, this method can provide important information regarding whether a subject has a particular disease, such as cancer. This method can be a basic screen whereby a biological sample from a subject is contacted by a lambody that is known to bind to a glycan, glycolipid or glycoprotein associated with the disease but not to normal cells or tissue. If the lambody is found to bind to the sample, a diagnosis of disease may be made. If desired, the amount of binding can be determined and the measured amount of binding can be compared to the amount bound in a control sample, where the control sample is a biological sample of the same source, but obtained from a subject that is known to not have the disease in question.

The methods for diagnosing a disease in a subject can also be adapted to provide more information regarding the disease, such as the extent or severity of the disease in the subject. For example, a biological sample from a subject can be contacted by a lambody that is known to bind to a glycan, glycolipid or glycoprotein associated with the disease but not to normal cells or tissue, and the amount of binding can be determined. The measured amount of binding can then be compared to the amount bound in one or more control samples, where the control samples were biological samples of the same source, but obtained from subjects known to have varying levels of the disease in question. In this manner, the method of diagnosis can be used to diagnose the degree or severity of the disease in question by comparison to controls.

The methods of the present invention further include methods for making a prognosis of a subject having a disease. Such methods comprise (a) contacting a biological sample from a subject having a disease with a lambody subunit, lambody or lambody multimer that binds a glycan, glycolipid or glycoprotein associated with the disease of the subject, (b) measuring the amount of lambody subunit, lambody or lambody multimer bound in (a), (c) comparing the amount measured in (b) with one or more amounts previously determined in control samples, and (d) making a prognosis of the subject based on the comparison in (c). These methods of making a prognosis are similar to the methods for diagnosing disease in a subject, but by comparing the amount of lambody bound to a biological sample to one or more control samples, where the control samples are from individuals with (i) known levels or degrees of disease and/or (ii) known rates of cure or death, a prognosis can be made for the subject in question.

The methods of the present invention additionally include methods for monitoring progression of disease in a subject. Such methods comprise (a) contacting a biological sample from a subject having a disease with a lambody subunit, lambody or lambody multimer that binds a glycan, glycolipid or glycoprotein associated with the disease of the subject, (b) measuring the amount of lambody subunit, lambody or lambody multimer bound in (a), and (c) comparing the amount measured in (b) with one or more amounts previously determined in a biological sample of the same source from the subject. By comparing the measured amounts of lambody in biological samples from a subject taken at two different points in time, such as before and after administration of a treatment, the course of the disease can be monitored in the subject. Such monitoring can provide important information such as whether the treatment is effective and whether the disease has recurred at some time after the treatment has been completed.

The methods of the present invention further additionally include methods for imaging a disease in a subject. Such methods comprise administering a labeled lambody subunit, lambody or lambody multimer to a subject and detecting the lambody subunit, lambody or lambody multimer in the subject, wherein the lambody subunit, lambody or lambody multimer binds a glycan, glycolipid or glycoprotein associated with the disease. These methods provided in vivo means that can be used in the diagnosis, making of a prognosis, and monitoring the progression of a disease in a subject. Such methods will be especially useful when a biological sample that would contain a glycan, glycolipid or glycoprotein associated with the disease cannot easily be obtained from the subject.

In each of the methods related to means for imaging, the means used to perform the imaging will depend on the manner in which the lambodies are labeled. As an example, when the lambodies are conjugated to a detectable label such as a radioactive marker, its presence and location in a subject can be detected and/or measured by standard imaging techniques. Other suitable detectable labels for using in the imaging methods include, but are not limited to, magnetic resonance imaging (MRI), positron emission tomography (PET), and optical imaging.

The methods of the present invention still further include methods for treating a subject having a disease. Such methods comprise administering a therapeutically-effective amount of a lambody subunit, lambody or lambody multimer to a subject having a disease, wherein the lambody subunit, lambody or lambody multimer binds a glycan, glycolipid or glycoprotein associated with the disease of the subject. The therapeutically-effective amount of a lambody will vary depending upon the physical characteristics of the subject, the severity of the subject's symptoms, the particular disease or condition being treated, the formulation and the means used to administer the lambody, the number of doses being administered to the subject over the course of treatment, and the method being practiced. The specific dose for a given subject is usually set by the judgment of the attending physician.

The lambodies administered to the subject in the methods of treatment may be one or more lambodies alone, where simple binding by the lambody to the glycan, glycolipid or glycoprotein is sufficient to treat the subject having a disease. Binding by the lambody may interfere with or block a cellular process required to achieve or maintain the disease state, for example, and thus treat the disease in the subject. Alternatively, or in addition, the lambodies administered to the subject having a disease may be a lambody that is conjugated to a therapeutic agent. In this alternative, the therapeutic agent will have activity against the diseased cells and thus treat the disease in the subject.

In each of the methods of the invention that includes a step of detecting lambody binding, the lambody may be detected by using a lambody that is conjugated to a detectable label (e.g., biotin, a fluorescent marker, radioactive marker), including the specific examples provided herein. When such labels are used, the lambody can be detected through the use of means relevant to the particular label.

The lambody may also be detected by using a secondary binding moiety that binds to the lambody that, in turn, is bound to its cognate antigen. For example, a conventional antibody, whether itself labeled or unlabeled, that specifically binds to the lambody may be used. If labeled, the conventional antibody can be labeled using one of the vast array of molecules that are commonly used to label antibodies, including each of the detectable labels discussed herein for lambodies. If unlabeled, a secondary antibody that is labeled may be used. The labeled secondary antibody will have binding specificity for the primary antibody, and may again be labeled using one of the vast array of molecules that are commonly used to label antibodies as discussed herein.

As a further option, the lambody may be detected by using a second lambody that also binds to the target glycan, glycolipid or glycoprotein bound by the first lambody (i.e., a sandwich assay). The second lambody may have binding specificity to the same glycan, glycolipid or glycoprotein, or it may have binding specificity to a different glycan, glycolipid or glycoprotein found on the same molecule. The second lambody will be labeled in any of the manners discussed herein. As an example of a detection means that uses primary and secondary lambodies, reference can be made to FIG. 9 which shows a primary lambody multimer (a capture lambody) bound to a fucosylated glycoprotein, which in turn is bound by a secondary lambody multimer (detection lambody), wherein the primary and secondary lambody multimers bind to different glycans of the fucosylated glycoprotein. Further, the secondary lambody multimer is a fusion protein dimer that bears the Fc region of mouse IgG which allows detection of the secondary lambody multimer using an anti-mouse IgG Fc antibody which itself can be labeled.

In one embodiment of the invention, the detectable label that may be conjugated to a lambody or antibody is an enzyme. When exposed to its substrate, the enzyme will react with the substrate in such a manner as to produce a chemical moiety which can be detected, for example, by spectrophotometric, fluorometric or by visual means. Suitable enzymatic tags include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

In another embodiment, the detectable label that may be conjugated to a lambody or antibody, is a radioactive marker. Use of a radioactive marker as the detectable label allows detection of the lambody or antibody through the use of radioimmune assays. The radioactive isotope can be detected by such means as the use of a gamma counter or a scintillation counter or by autoradiography. Isotopes which are particularly useful for the purpose of the present invention include, but are not limited to, $^{3}$H, $^{131}$I, $^{35}$S, $^{14}$C, and $^{125}$I.

In further embodiment, the detectable label that may be conjugated to a lambody or antibody is a fluorescent marker. When the fluorescently-labeled lambody or antibody is exposed to light of the proper wave length, its presence can then be detected due to fluorescence. The fluorescent markers include, but are not limited to, CYE dyes, fluorescein isothiocyanate, rhodamine, phycoerytherin, phycocyanin, allophycocyanin, o-phthaldehyde and fluorescamine.

In still a further embodiment, the detectable label that may be conjugated to a lambody or antibody is a fluorescence-emitting metals such as $^{152}$Eu, or others of the lanthanide series. These metals can be attached to the lambody or antibody using such metal chelating groups as diethylenetriaminepentaacetic acid (DTPA) or ethylenediaminetetraacetic acid (EDTA).

In again a further embodiment, the detectable label that may be conjugated to a lambody or antibody is a chemiluminescent marker. The presence of the chemiluminescent-lambody or antibody is determined by detecting the presence of luminescence that arises during the course of a chemical reaction. Examples of particularly useful chemiluminescent labeling compounds include, but are not limited to, luminol, luciferin, isoluminol, theromatic acridinium ester, imidazole, acridinium salt and oxalate ester.

Means for detecting the labeled lambodies and antibodies include immunoassays, such as enzyme-linked immunoabsorbent assay (ELISA; including sandwich ELISA and competitive ELISA), radioimmunoassay (RIA), immunoradiometric assay (IRMA), Western blotting, immunofluorescence (both primary (or direct) and secondary (or indirect)), flow cytometry (including fluorescence-activated cell sorting (FACS)), and immunochemistry.

Immunochemistry techniques include immunohistochemistry ("IHC") and immunocytochemistry ("ICC"). IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of specific lambodies, wherein the lambodies are used to specifically target molecules inside or on the surface of cells. The lambody is typically conjugated to a detectable label that will undergo a biochemical reaction, and thereby experience a change color, upon encountering the targeted molecules. In some instances, signal amplification may be integrated into the particular protocol, wherein a labeled secondary binding moiety, that includes a marker stain, follows the application of a lambody. Immunohistochemical assays are known (e.g., Jalkanen, et al., J. Cell. Biol. 101:976-985 (1985); Jalkanen, et al., J. Cell. Biol. 105:3087-3096 (1987). For immunohistochemistry, tissue sections are generally obtained from a patient and fixed by a suitable fixing agent such as alcohol, acetone, and paraformaldehyde, to which is reacted a lambody. Biological samples appropriate for such detection assays include, but are not limited to, cells, tissue biopsy, whole blood, plasma, serum, sputum, cerebrospinal fluid, pleural fluid, urine and the like. Alternatively, immunocytochemistry may be utilized. In general, cells are obtained from a patient and fixed by a suitable fixing agent such as alcohol, acetone, and paraformaldehyde, to which is reacted a lambody. Methods of immunocytological staining of human samples is known to those of skill in the art and described, for example, in Brauer et al., 2001 (FASEB J, 15, 2689-2701), Smith-Swintosky et al., 1997 (J Neurochem. 69(5):1890-6)).

In each of the methods of the invention that includes a step of detecting a lambody, the lambody may be free or bound to an immobilized surface. As such, the lambody can be added directly to a sample obtained from a subject, or the sample can be applied to an immobilized surface which displays the lambody, such as an array, micro-array or chip that bears a variety of lambodies at known positions.

In each of the methods of the invention, the biological sample may be, but is not limited to, a bodily fluid, secretion, excretion, cells, tissue, and tissue biopsy. Specific examples include, but are not limited to, whole blood, plasma, serum, mucus, cerebrospinal fluid, pleural fluid, urine, tears, saliva, sputum and stool.

In each of the methods of the invention related to means for diagnosing or making a prognosis, the disease may be any in which a selected glycan, glycolipid or glycoprotein can be used to distinguish between a healthy and diseased state. For example, the disease may be one that is characterized by expression of certain glycans, glycolipids or glycoproteins in diseased tissue and the absence or decreased expression of the glycans, glycolipids or glycoproteins in normal tissue. One can then make certain conclusions regarding the disease based on the level of expression of the glycans, glycolipids or glycoproteins in a biological sample that includes the diseased tissue. The presence or absence of the glycans, glycolipids or glycoproteins can be used to make a diagnosis of disease. The particular level of the glycans, glycolipids or glycoproteins, or changes in the level over time, can be used to make a prognosis regarding the disease.

Similarly, in each of the methods of the invention related to means for treating or imaging, the disease may again be any in which a selected glycan, glycolipid or glycoprotein can be used to distinguish between a healthy and diseased state. For example, the disease may be one that is characterized by expression of certain glycans, glycolipids or glycoproteins in diseased tissue and the absence or decreased expression of the glycans, glycolipids or glycoproteins in normal tissue. One can then use this distinction to ensure that only diseased tissue is being treated or imaged.

With respect to each of the methods of the present invention related to the diagnosis, making a prognosis, monitoring progression, treating or imaging, the disease may be, but is not limited to, a disease, condition or, in particular, cancer. Particular conditions include, but are not limited to, tonsillitis and chronic tonsillitis. Particular types of cancer include, but are not limited to, carcinoma, including but not limited to adenocarcinoma, squamous cell carcinoma, adenosquamous carcinoma, anaplastic carcinoma, large cell carcinoma, small cell carcinoma, and cancer of the skin, breast, prostate (prostate adenocarcinoma), bladder, vagina, cervix, uterus, liver, kidney, pancreas, spleen, lung (lung carcinoma, lung adenocarcinoma), trachea, bronchi, colon (colon adenocarcinoma), small intestine, stomach, esophagus, gall bladder; sarcoma, including but not limited to chondrosarcoma, Ewing's sarcoma, malignant hemangioendothelioma, malignant schwannoma, osteosarcoma, soft tissue sarcoma, and cancers of bone, cartilage, fat, muscle, vascular, and hematopoietic tissues; lymphoma and leukemia, including but not limited to mature B cell neoplasms, such as chronic lymphocytic leukemia/small lymphocytic lymphoma, B-cell prolymphocytic leukemia, lymphomas, and plasma cell neoplasms, mature T cell and natural killer (NK) cell neoplasms, such as T cell prolymphocytic leukemia, T cell large granular lymphocytic leukemia, aggressive NK cell leukemia, and adult T cell leukemia/lymphoma, Hodgkin lymphomas, and immunodeficiency-associated lymphoproliferative disorders; germ cell tumors, including but not limited to testicular and ovarian cancer; blastoma, including but not limited to hepatoblastoma, medulloblastoma, nephroblastoma, neuroblastoma, pancreatoblastoma, leuropulmonary blastoma and retinoblastoma. The term also encompasses benign tumors.

When the disease is cancer, the methods can be used to grade the particular stage of a cancer, including Stages 0-IV; Primary Tumor (T) stages TX, T0, Tis, T1, T2, T3, and T4; Regional Lymph Nodes (N) stages NX, N0, N1, N2, and N3; Distant Metastasis (M) stages MX, M0, and M1; and used in tumor grading.

As used herein the subject is a human or non-human animal, e.g., a non-human primate, bird, horse, cow, goat, sheep, a companion animal, such as a dog, cat or rodent, or other mammal.

Pharmaceutical Compositions

Each of the lambody subunits, lambodies and lambody multimers of the present invention can be formulated in a pharmaceutical composition that is suitable for administration to a subject. Such pharmaceutical compositions may be administered to a subject in the various methods of the present invention as an alternative to directed administration of the lambodies to the subject. The pharmaceutical compositions comprise one or more lambodies and optionally a pharmaceutically acceptable diluent, carrier, and/or excipient, such as a buffer, a surfactant, a dispersing agent, a preservative, a solubilizing agent, and isotonicity agent, or any other pharmacologically inert vehicle for delivering the lambodies of the invention to a subject. Conventional techniques for preparing pharmaceutical compositions are disclosed, for example in: Remington, The Science and Practice of Pharmacy, 19th ed., Gennaro, Ed., Mack Publishing Co., Easton, Pa. 1995.

Example 1

Practically all types of human tumor cells express glycoproteins with aberrant glycosylation patterns (Varki et al., 2009; Almogren et al., 2012). The best studied cancer-specific carbohydrates are truncated O-glycans such as the T-nouvelle antigen (Tn, GalNAcα1-Ser/Thr) and TFα (Galβ1-3GalNAcα1-Ser/Thr), both considered pancarcinoma antigens that uniquely decorate mucin-type glycoproteins in about 90% of human cancer cells, but are distinctly absent from nearly all normal tissues.

Isolation of Lambodies Reactive to Tumor-Associated Carbohydrate Antigens.

A library of yeast surface-displayed (YSD) lamprey variable lymphocyte receptors (VLRs) was screened for clones that can selectively bind chosen glycoproteins and/or glycans. Clones that can bind TFα were isolated from a library of $1.2 \times 10^8$ independent clones (Tasumi et al., 2009) using as antigen a synthetic polyacrylamide (PAA) glycoconjugate of TFα. The first batch of clones that was isolated could discriminate between TFα and TFβ. TFβ is the Galβ1-3GalNAcβ anomeric structure of the GM1 ganglioside, which is expressed in a variety of normal human cells, including natural killer cells that are important immune effector cells. These clones were then tested for binding of asialo-glycophorin A (aGPA), a human erythrocyte membrane glycoprotein whose native form is decorated with 16 sialyl-TFα structures (Pisano et al., 1993). Most of the anti-TFα clones were poor binders of aGPA, and those that did bind failed to discriminate between aGPA and native GPA, indicating binding to sialylated TFα structures that are common carbohydrate structures in normal mucin-type glycoproteins. For detection of tumor-associated carbohydrate antigens, isolation of clones with reactivity for desialylated TFα and non-reactivity to TFβ was needed.

Figure 2:
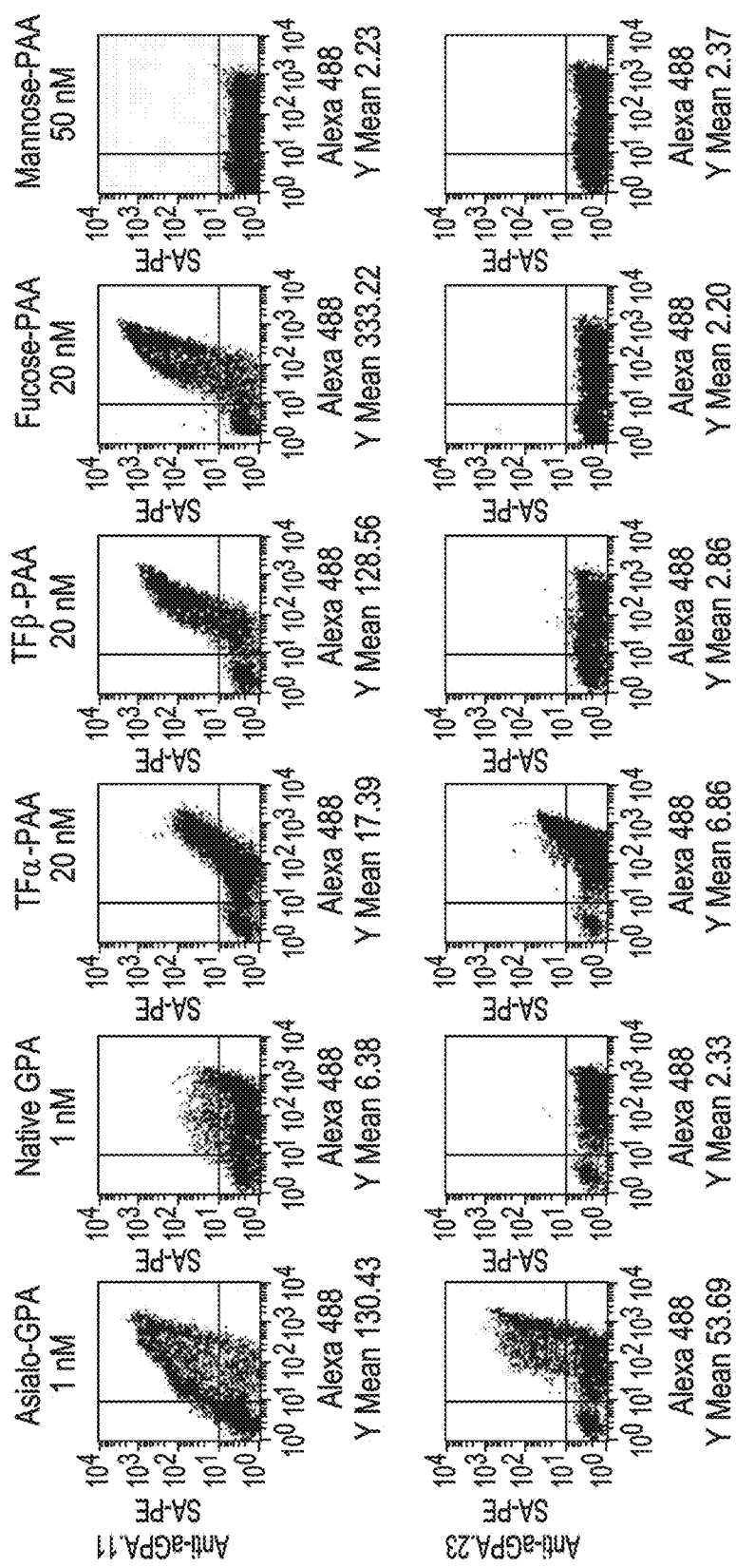
FIG. 2. Flow cytometry analysis of glycoconjugate selectivity for two anti-aGPA VLR clones. Dot-plot presentation of labeling intensities, and measurement of the Y-mean fluorescence intensities from ligand binding for asialo-GPA, GPA, TFα-PAA, TFβ-PAA, fucose-PAA and mannose-PAA, used to label at the indicated concentrations (Y-mean<3 indicates no binding). All antigens were biotinylated and were detected with Phycoerythrin-conjugated Streptavidin (SA-PE). The synthetic glycans were polyacrylamide (PAA) conjugates. The level of VLR surface display was detected by labeling with a rat anti-FLAG mAb followed by anti-rat Alexa 488 antibodies.
Figure 3:
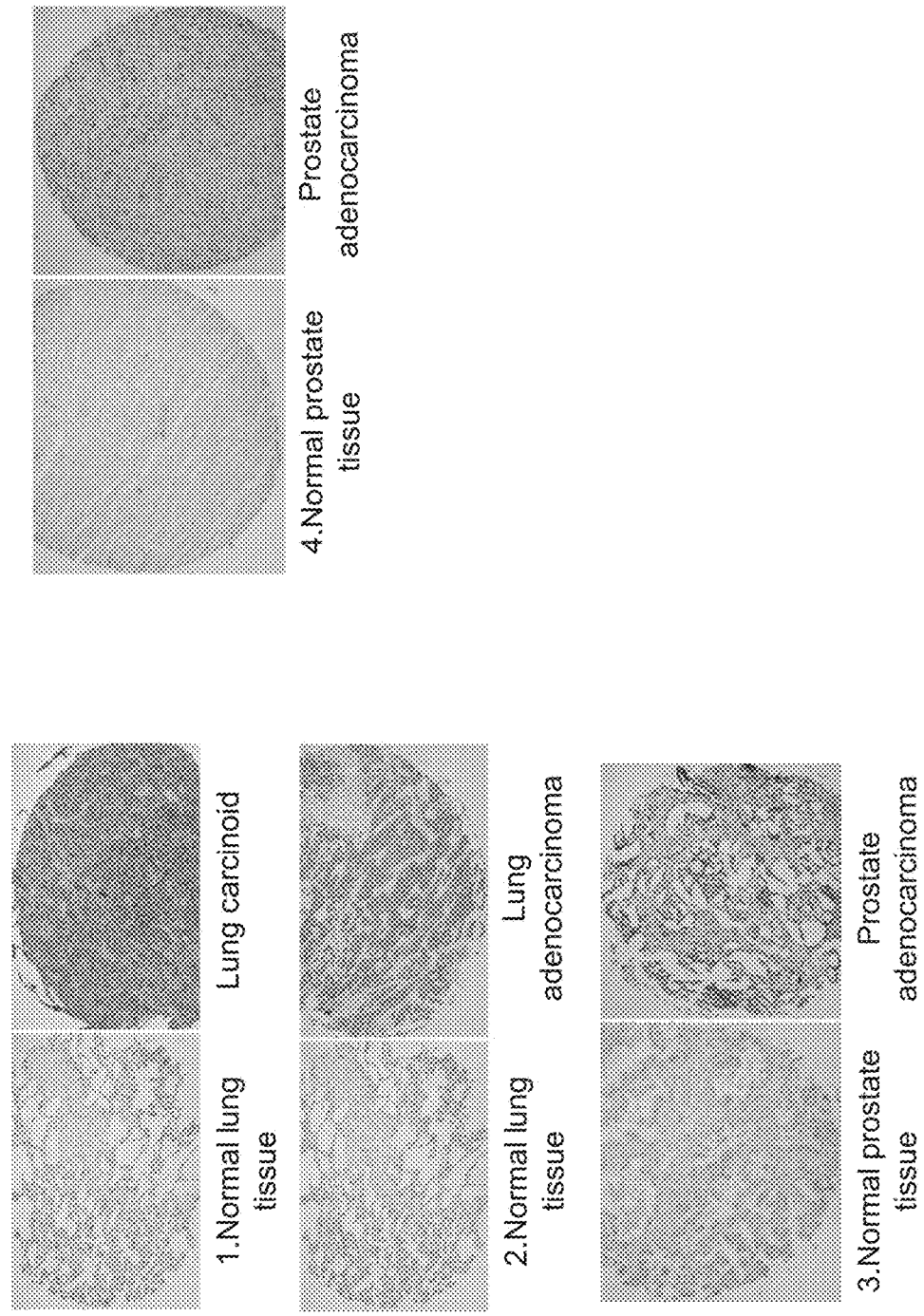
FIG. 3. Lambody staining of human normal and cancer tissues. 1. Normal lung and lung carcinoma. 2. Normal lung and lung adenocarcinoma. 3. & 4. Normal prostate and prostate adenocarcinoma. Tissue microarray slides were incubated with 5 µg/mL of VLRB.aGPA.23-mFc overnight at 4° C., and immune complexes were detected with anti-mouse IgG-HRP and DAB substrate (brown), then counterstained with Hematoxylin (blue). Photos were taken at 5× magnification.

To improve the likelihood of obtaining glycan binders with tumor reactivity, the antigens TFα and aGPA were alternated in consecutive rounds of enrichment. TFα was used for the first of two rounds of magnetic-activated cell sorting (MACS) and for the first of two rounds of fluorescence-activated cell sorting (FACS), switching to aGPA in the second MACS and in the final FACS, when individual clones were sorted. This strategy resulted in clones with the desired selectivity for aGPA over native GPA. Nine of the 15 clones sequenced were of unique sequence (60%) and one of these, VLRB.aGPA.23, showed high selectivity for both aGPA and TFα, whereas most other clones were less specific, binding also TFβ and fucose, which is another glycan used in the initial assessment of selectivity for these clones (FIG. 2).

Lambody Staining of Human Cancer Tissue Microarrays.

The ability of VLRB.aGPA.23 to recognize tumor-associated glycans as they are presented in tissues was tested by immunohistochemistry (IHC) with human tissue microarrays (TMA). This lambody stained 14 out of 34 different types of adenocarcinomas and squamous cell carcinomas (41%), including those of the bladder, breast, cervix, cheek, colon, esophagus, greater omentum, larynx, liver, lung, nose, nasopharynx, ovary and tongue. Staining with VLRB.aGPA.23 was undetectable in nearly all normal or benign tissues (FIGS. 3 & 4A-4H), except for one case of staining in a small portion of tumor-adjacent normal lung tissue. In tumor tissues various levels of membrane and cytoplasmic staining were visible in discrete portions of the tumors, indicating specific recognition of tumor antigens. Three other clones from this screen were tested by IHC, but these either stained normal tissues as well as tumors, or produced faint and diffuse staining patterns.

Figures 5A, 5B:
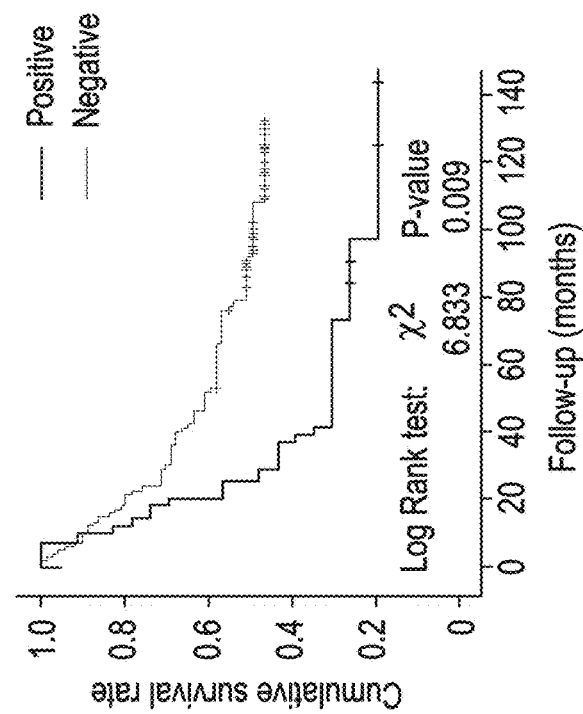
FIGS. 5A-5B. Detection of human lung cancers with VLRB.aGPA.23.

A cohort of tissue samples from 103 lung cancer patients was focused on (FIG. 5A), of which 27% stained positive with VLRB.aGPA.23, as determined by digital scanning and quantitative analysis of the fractions of cells that stained positive (see Methods). Among these patients, 88 were diagnosed with non-small cell lung cancer (NSCLC), and those whose tumors stained positively with VLRB.aGPA.23 at medium to high intensities (27%), had a significantly poorer overall survival rate (FIG. 5B).

Binding Selectivity of Lambody VLRB.aGPA.23.

Figure 6:
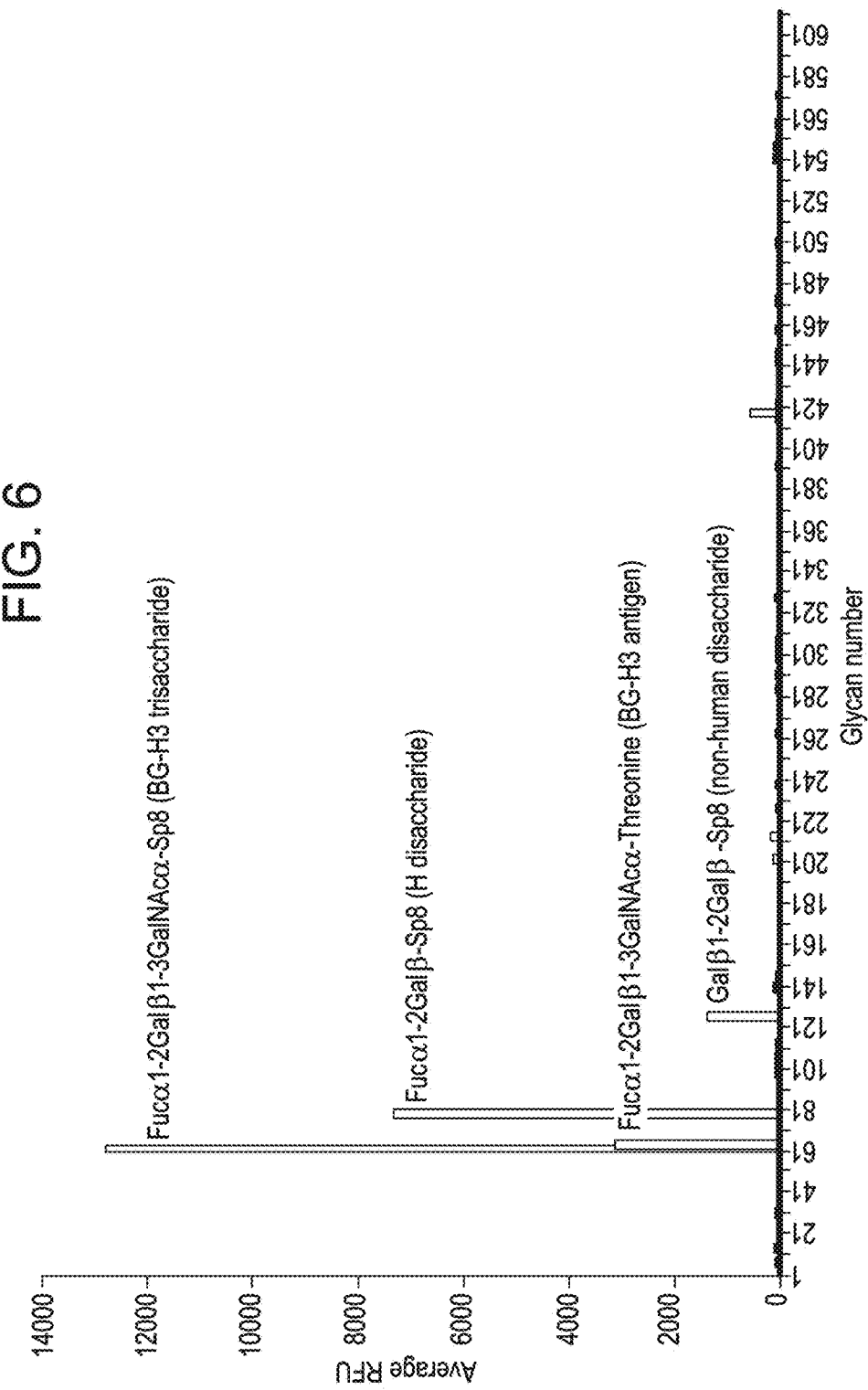
FIG. 6. Glycan binding profile of VLRB.aGPA.23 showing the four main glycan structures recognized. The CFG array V5.0, consisting of 611 printed glycans, was stained with 2 µg/mL lambody.

Optimal carbohydrate ligands were profiled and the selectivity of VLRB.aGPA.23 was assessed using two printed glycan microarrays. One array, from the Consortium for Functional Glycomics (CFG) (Blixt et al., 2004), consisted of 611 glycan structures. Blood group H type 3 trisaccharide (BG-H3, Fucα1-2Galβ1-3GalNAcα) and the H disaccharide (Fucα1-2Galβ) were the main reactive structures (FIG. 6). The second array consisted of 215 neoglycoproteins and glycoproteins (Oyelaran et al., 2009), and the structures giving the highest signals were predominantly aGPA and glycopeptides containing TFα-Serine. In agreement with the selection data, no binding to GPA and very weak binding to TFβ were observed on this array. TFα-Serine was not present on the CFG array, and BG-H3 and the H disaccharide were not present on the second array.

The large collection of glycans and the complementary diversity on the two arrays provided detailed structural information on the binding specificity of VLRB.aGPA.23. The preferred ligand for this lambody appeared to be BG-H3, a fucosylated TFα structure. Although the H disaccharide was also bound, other fucosylated blood group H antigens, including blood group H1, H2, H4, and H6, were not recognized on the arrays, nor were extended structures, such as blood group A or blood group B. The Galβ1-3GalNAcα disaccharide (TFα substructure) lacking the terminal fucose was also recognized, but only when attached to a serine. The disaccharide fragment alone (not attached to serine; Galβ1-3GalNAcα-Sp8 or Sp16) was bound only very weakly by the lambody, and this disaccharide was not recognized at all when attached to threonine (Galβ1-3 GalNAcα-Sp14). These factors indicated that the moiety at the reducing end of both BG-H3 and TFα structures has a significant influence on recognition. Consistent with this analysis, BG-H3 trisaccharides attached to oligosaccharide chains, for example Fucα1-2Galβ1-3GalNAcα1-3(Fucα1-2)Galβ1-4Glcβ-Sp0, were not bound by the lambody. In addition, BG-H3 attached to a threonine (Fucα1-2Galβ1-3GalNAcα-Sp14) displayed reduced binding as compared to a simple linker (Fucα1-2Galβ1-3GalNAcα-Sp8). Taken together, these data indicate that the optimal ligand is most likely BG-H3 attached to a serine. Since this structure was not present on either array, this hypothesis will remain to be tested in future studies. Nevertheless, the glycan array data demonstrates that VLRB.aGPA.23 possesses a high degree of selectivity for BG-H3 and TFα-Serine glycans. Although there was some cross-reactivity with other glycans (e.g. the non-human structures Galβ1-2Galβ-Sp8 and Galβ1-6Manα), the overall selectivity of this lambody was better than most naturally-occurring lectins and antibodies (Manimala et al., 2006, 2007). For example, mAb JAA-F11, an anti-TFα IgG, was profiled with a CFG microarray of 200 glycans and shown to react mainly with four structures. These were TFα, the core-2 trisaccharide [Galβ1-3(GlcNAcβ1-6)GalNAcα], 6-sialyl-TFα [Galβ1-3(Neu5Acβ2-6)GalNAcα], and 6-LacNAc-Tn [Galβ1-

4GlcNAcβ1-6GalNAcα] (Chaturvedi et al., 2008). Lambody VLRB.aGPA.23 reacted with a narrower spectrum of related structures, and was non-reactive to sialyl-TFα, which is a common O-glycan in normal mucin-type glycoproteins.

Binding Affinity of Lambody VLRB.aGPA.23.

Figure 7:
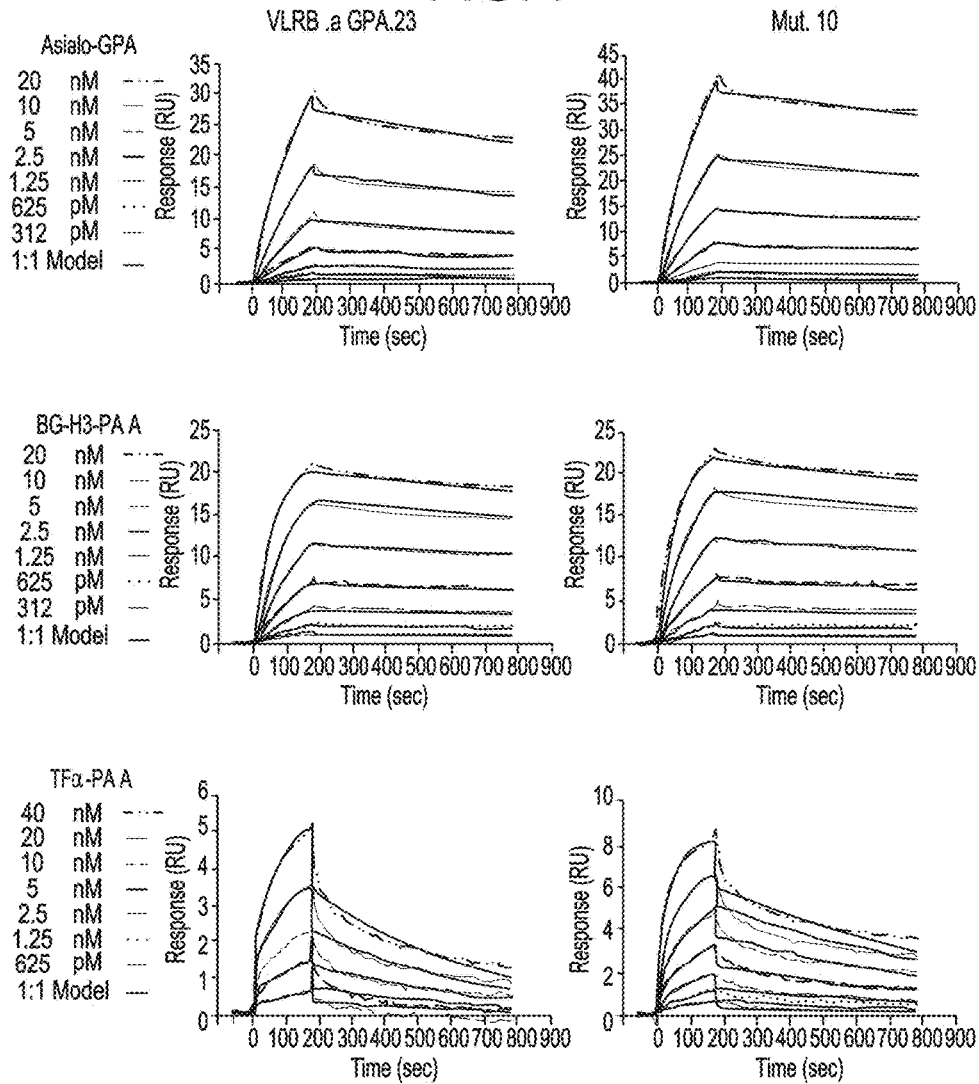
FIG. 7. Kinetic analysis of glycoconjugates binding by VLRB.GPA.23 and affinity improved clone Mut. 10. Representative SPR sensorgrams for the interaction of immobilized lambodies with aGPA, BG-H3-PAA and TFα-PAA, are shown for concentrations of 0.3125, 0.625, 1.25, 2.5, 5, 10, 20 and 40 nM. Reference subtracted and blank subtracted binding data were fitted with a 1:1 Langmuir binding model to determine the association and dissociation constants. The equilibrium dissociation constants were calculated from these values. The statistics for Chi-squared and U-values are shown, and all T-values for ka, kd and Rmax were >100.

To further evaluate the affinity and selectivity of VLRB.aGPA.23, surface plasmon resonance (SPR) was used to measure binding of aGPA, TFα and BG-H3. The lambody was captured via an anti-His tag mAb immobilized on the surface of the Biacore sensor chip (FIG. 7). At concentrations of glycoconjugates from 156 pM to 40 nM, the binding kinetics were found to fit very well a 1:1 Langmuir model ($\chi^2 \leq 0.13$, T-values>100, U-values≤4), with calculated affinity constants of $2.1 \times 10^{-10}$ M for BG-H3, $1.1 \times 10^{-9}$ M for aGPA and $7.8 \times 10^{-9}$ M for TFα. Such a high affinity for carbohydrate antigens is remarkable, especially since this lambody originated from unstimulated naïve lamprey.

Affinity Maturation of VLRB.aGPA.23.

In order to improve the affinity of this lambody for TFα, we performed one round of in vitro affinity maturation by random mutagenesis of the DNA coding for VLRB.aGPA.23, and selected clones with improved binding. The best mutant clone, Mut. 10, revealed 5-fold higher affinity for TFα and 1.7-fold for aGPA. For both of these ligands, accelerated association and decreased dissociation rates contributed to the improvement (FIG. 7). Clone Mut. 10 differed from VLRB.aGPA.23 (SEQ ID NO:2) at five residue positions: S19N, S86G, H105R, K112M and T208S. However, only two of these mutations, S86G and K112M, are at or near the predicted glycan-binding site of VLRB.aGPA.23, based on the crystal structure of a VLRB bound to blood group H type 2 trisaccharide (BG-H2, Fucα1-2Galβ1-4GlcNAcβ) (Han et al., 2008). Accordingly, these two mutations probably account for improved binding to TFα, whereas the other three, S19N, H105R and T208S, may have been selected for other reasons (e.g., because they increased surface expression of VLRB.aGPA.23).

A General Approach for Selection of Glycan-Binding VLRs.

In order to evaluate the generality of the approach described herein, the VLR YSD library was surveyed for binders of additional synthetic glycoconjugates and glycoproteins that display important biomedical glycotopes. These included monosaccharides such as mannose, the Tn pancarcinoma antigen (GalNAcα), and N-glycolylneuraminic acid (Neu5Gcα), a dietary-derived hydroxylated form of N-acetylneuraminic acid (Neu5Ac) that can cause chronic inflammation and carcinomas. Among the disaccharides, TFα was used, and from the trisaccharides, Lewis A [Galβ1-3(Fucα1-4)GlcNAcβ] and Lewis X [Galβ1-4(Fucα1-3)GlcNAcβ] were used, whose uniquely sialylated forms are characteristic of most cancer cells (Kannagi, 2007). As an example, for polysaccharides poly-Man-9, a unique glycan of the HIV viral envelope, and its glycoprotein carrier gp120 were selected (Wyatt et al., 1998). Another glycoprotein target was asialo-ovine submaxillary mucin (aOSM), whose native form consists of 50% carbohydrates, mostly sialyl-Tn (94%) and TFα (4%). Clones were isolated that can bind these target glycotopes and batches of 8-24 clones per target were sequenced. In each case, 75-100% of the clones had unique sequences. As shown in FIGS. 8A-8H for one representative from each screen, these clones bind their cognate ligands in a glycan-dependent manner. None of the clones reacted with the backbone spacer-PAA, nor with mannose except for the anti-Mannose clone. The anti-TFα clone was non-reactive to TFβ, the anti-Neu5Gc only reacted with Neu5Gc, not with Neu5Ac, and the anti-Lewis A and anti-Lewis X were not cross-reactive. Alternating between poly-Man-9 and gp120 as antigens in consecutive cycles of enrichment enabled isolation of clones with excellent affinity both for gp120 and Man-9.

Discussion

All the glycan-binding VLR clones described here were isolated from a modest sized YSD library of $10^8$ independent clones, which was constructed from lymphocyte RNA and genomic DNA of around one hundred lamprey larvae and adults. These lamprey were collected in the wild and were not challenged specifically with any of these glycoconjugates in order to produce an immune library (Tasumi et al., 2009). Nonetheless, simple procedures allowed isolation from this library of good, as well as some excellent, binders for each of the biomedically important glycotope targets screened. For this survey, only small batches of 10-40 clones per target glycotope were sampled and assayed for selectivity, from amongst populations of thousands of positive clones that were sorted, which based on the pilot sequencing samples should consist mostly of unique clones (60-100%). This demonstrates that the library consists of large populations of highly diverse VLR clones that can bind each of the glycotopes, and likely other glycotope of interest.

On the surface of yeast, monomeric VLRs are displayed at densities that can enable cooperative binding by several VLRs of multivalent antigens, such as most glycoconjugates, generating stable complexes due to the high avidity. This is similar to the mode of binding of most high affinity lectins, which are typically multimeric proteins with multiple binding sites, and pentameric IgM antibodies that are the common type of glycan-binding antibodies, with affinities typically in the range of $10^{-5}$ to $10^{-6}$ M. In contrast, the dimeric lambodies described here are either VLR-Fc fusion proteins, analogous to IgGs, or the compact VLR-GCN4 fusion proteins, and yet many of these could retain in solution their high affinity for glycoconjugates. For example, lambody VLRB.aGPA.23 binds BG-H3, aGPA and TFα with dissociation constants of 0.2, 1 and 8 nM, respectively, an affinity that rivals most, or perhaps even all naturally occurring lectins, as well as conventional and recombinant antibodies. For comparison, a multimeric anti-TFα scFv had dissociation constants for aGPA of 88 and 220 nM for the tetrameric and trimeric forms of the antibody, respectively (Ravn et al. 2007); the antiviral lectin griffithsin binds carbohydrates of gp120 with a dissociation constant of 8 nM (Moulaei et al., 2010); and a pentameric IgM antibody was developed with the exceptionally high affinity constant of 200 pM for a glycopeptide epitope in aGPA (Karsten et al., 2010).

Previously, in vitro affinity maturation of VLRs reactive to the protein lysozyme were reported, with up to 100-fold improvement following random mutagenesis, and 1,300-fold improvement following targeted mutagenesis (Tasumi et al., 2009). Here, a single cycle of random mutagenesis of VLRB.aGPA.23 was performed, which resulted in 5-fold improvement in binding of TFα, with affinity constant of 1.6 nM. This improvement demonstrates that lambodies can also be evolved in vitro to achieve higher affinity for glycans, which sets them apart from lectins and recombinant antibodies that only rarely have been successfully engineered for higher affinity and selectivity (Powlesland et al., 2009).

The assays to define the carbohydrate specificity of VLR-B.aGPA.23 indicated both BG-H3 and TFα-Serine structures are the main determinants recognized by this lambody from amongst hundreds of structures that were presented on two glycan arrays. It is likely this lambody is selective for an epitope that includes both elements of the TFα and blood group H structures. Extension of the TFα to the BG-H3 Fucα1-2 should be possible based on the crystal structure of the VLRB-BG-H2 trisaccharide complex (Han et al., 2008). Assuming a similar glycan-binding site for VLRB.aGPA.23, it should be able to accommodate either TFα or fucosylated TFα, with about 40-fold tighter binding of the latter due to additional contacts with the VLR, as shown by SPR. Furthermore, on glycan arrays TFα-Serine was a good ligand, TFα disaccharide was weaker but TFα-Threonine was not recognized, and binding to BG-H3-Threonine was 4-fold weaker than to BG-H3. This may indicate preference of this lambody for the particular glycan-linkage conformational rotamer of serine over that of threonine, which may be different, as previously shown for GalNAcα attached to serine and threonine (Corzana et al., 2007).

Hundreds of human tissue samples were stained with VLRB.aGPA.23 and high specificity for tumor antigens was observed. VLRB.aGPA.23 stained with medium to high intensity 27% of lung cancer tissues, with undetectable levels practically in all normal lung tissues. This indicates that aberrantly glycosylated glycoproteins can be detected with highly selective lambodies. Importantly, the NSCLC patients whose lung tumors stained with moderate or high intensity with this lambody, had a significantly worse overall survival rate compared to those whose tumors stained negative or at low intensities, suggesting these abnormalities may be associated with the aggressive behaviors of the tumors. This lambody might be used to target tumors expressing BG-H3 antigens, as aberrant expression of the ABH antigens is often observed in oncogenesis of various organs (Le et al., 2001). For example, it has been reported that the normal colon mucosa expressed only BG-H1 antigen, whereas aberrant expression of BG-H2 with, or without BG-H3/4 antigens, was observed in several cancers of the proximal and distal colon (Fujitani et al., 2000a). The same group reported that BG-H1 and BG-H3/4 antigens were expressed in the normal human lung in apical surfaces of the bronchial epithelium (Fujitani et al., 2000b), but later it was realized that the IgM mAb MBr1 used to detect BG-H3/4 antigens, reacts mainly with the glycolipid globo H structure (Fucα1-2Galβ1-3 GalNacβ1-3Gal), which includes the BG-H4 antigen (Fucα1-2Galβ1-3GalNAcβ), but may not be able detect the O-linked BG-H3 antigen. Lambody VLRB.aGPA.23 may be a useful tool in deciphering the role of its carbohydrate antigen in the pathology of cancer cells.

Methods

Antigens.

The following antigens were used in Example 2, each of which was purchased from Glycotech (Gaithersburg, Md.):
  α-L-Fucose-PAA-biotin
  Galβ1-3GalNAcα-PAA-biotin (TFα)
  Galβ1-3GalNAcα-PAA (TFα)
  Galβ1-3GalNAcβ-PAA-biotin (TFβ)
  α-GalNAc-PAA-biotin (Tn)
  H(type 3)-PAA (BG-H3)
  Le$^a$-PAA-biotin
  Le$^x$-PAA-biotin
  α-D-Mannose-PAA-biotin
  α-Neu5Ac-PAA-biotin
  Neu5Gcα-PAA-biotin
  control spacer-PAA-biotin Core gp120 3.1 YU2 was a kind gift from Dr. George Lewis, and poly-Man-9-biotin from Dr. Lai-Xi Wang (IHV, UMB). Human glycophorin A, bovine submaxillary mucin and ovine submaxillary mucin (Sigma) were desialylated by mild acid treatment with 0.025 N $H_2SO_4$ in 0.85% NaCl, for 2 hours at 80° C., then neutralized with 1 M Tris-HCl pH 8.8 and dialyzed overnight against PBS pH 7.4 (QBI, Gaithersburg, Md.). Proteins were biotinylated with EZ-Link NHS-$PEO_4$-Biotinylation Kit (Pierce) at one to three moles biotin per mole protein.

YSD Library Screening.

A library of $1.2 \times 10^8$ independent clones was screened (Tasumi et al., 2009). To increase the sensitivity of detection, yeast library cells were treated with Endo Hf in buffer G5 (NEB) with 0.05% Tween 20, and 5,000 units Endo H per $OD_{600}$ of cells, shaking for 1 hour at 30° C. Antigen-binding clones were initially enriched by two rounds of MACS, using biotinylated antigens. For the glycoconjugate screens, 500 nM of each glycan-PAA were used for MACS and for sorting individual clones. For the anti-aGPA screen, the first MACS was done with 500 nM TFα-PAA, the second MACS with 500 nM aGPA, then sorting with 500 nM TFα-PAA and sorting again individual clones with 100 nM aGPA. For the anti-gp120 screen, the first MACS was done with 500 nM poly-Man-9, then MACS with 100 nM gp120, then sorting with 20 nM poly-Man-9 and sorting again individual clones with 1 µM gp120. The nucleic acid and amino acid sequences of one lambody with binding specificity for pg120 are provided in SEQ ID NOs:3 and 4, respectively. For the anti-aOSM screen, 5 µg/ml asialo-BSM was used for the first MACS and 140 ng/ml aOSM for the second MACS and for sorting. For the MACS, anti-biotin microbeads and MiniMACS separation unit were used (Miltenyi). For staining and washing a buffer made of PBS pH 7.4, 0.5% BSA, 2 mM EDTA and 0.1% Tween 20 was used. For sorting, the VLRs were labeled with 100 ng/mL of rat anti-FLAG (Stratagene). The cells were rotated for 25 min at room temperature then placed on ice for 5 min, washed 3 times and incubated with 1:1,000 dilutions of Alexa Fluor-488 donkey anti-rat IgG (Invitrogen) and Streptavidin-Phycoerythrin (SA-PE, Invitrogen) for 20 min on ice. Cells were washed 3 times with PBS, 0.1% BSA, and sorted using a FACSort equipped with a Cell Concentration Module (BD Biosciences). Data collection and analysis was with Cell-Quest Pro software (BD Biosciences). VLRB.aGPA.23 was deposited in GenBank, accession number JX123422. The nucleic acid and amino acid sequences of VLRB.aGPA.23 are provided in SEQ ID NOs: 1 and 2, respectively.

Lambody In Vitro Mutagenesis.

The VLRB.aGPA.23 DNA (SEQ ID NO: 1) served as template for PCR with GeneMorph II (Stratagene), and a mutant library was constructed in pYSD3 as reported (Tasumi et al., 2009). The mutant library of $6.7 \times 10^7$ independent clones was screened for improved TFα binders, first by MACS with 200 pM aGPA, followed by second MACS with 20 pM TFα. Individual clones labeled with 400 pM TFα were then sorted. The VLR inserts of the best 4 clones were sequenced, resulting in 3 unique clones that differed by 3-5 residues from VLRB.aGPA.23.

Yeast Secreted Lambodies.

The murine IgG2a Fc region from clone PS100053 (OriGene, Rockville, Md.) was cloned in pSCS2-α (Tasumi et al., 2009) downstream from the SfiI cloning sites, retaining the 6-His and FLAG tags, resulting in plasmid pα-mIgG2a-Fc. Fusion proteins are homodimers of about 96-106 kDa. A compact dimeric lambody format of about 56-67 kDa was constructed by replacement of the Fc region, immediately downstream from the IgG hinge, with the leucine zipper dimerization domain from the yeast GCN4 protein (Stefan et al., 2011), resulting in plasmid pα-GCN4.

Yeast strain YVH10 was used for secretion of lambodies, for 96 h at 30° C. in BYPDG pH 6.7 (2% Bacto Peptone, 1% Bacto Yeast Extract, 44 mM Na$_2$HPO$_4$.7H$_2$O, 56 mM NaH$_2$PO$_4$, 2% glucose, 2% galactose, 0.05% Tween 20, 100 µg/mL G418), with 2-4% galactose added daily (Tasumi et al., 2009). Lambodies were purified from secretion supernatants using Ni-NTA agarose (QIAGEN). Protein concentrations were determined using a Micro BCA Protein Assay Kit (Pierce). Typical yields of lambodies expressed in pα-mIgG2a-Fc were 2-5 mg/L, and 5-10 mg/L from pα-GCN4 clones.

Immunohistochemistry.

Tissue microarrays (TMAs) consisting of formalin-fixed and paraffin-embedded human tissue cores were purchased from US Biomax (Rockville, Md.), Pantomics (Richmond, Calif.) and IMGENEX (San Diego, Calif.). IMGENEX TMAs IMH-305 and IMH-358 were available with lung cancer patient survival data. Standard IHC protocol was followed. Briefly, TMAs were deparaffinized by several changes of xylene for a total of 30 min. The slides were then rehydrated in gradual ethanol before immersion in PBS pH 7.4. Endogenous peroxidase was quenched by 20 min incubation in 3% H$_2$O$_2$ in methanol. Antigen retrieval was performed by immersion in 1 mM EDTA pH 8.0, for 10 min at 96° C. in a water bath. Slides were blocked with 10% normal horse serum (Invitrogen), 1% BSA (Pierce), for 1 hour at room temperature. The lambodies, as fusion proteins with the mouse IgG2a Fc region, were diluted to 5 µg/mL in PBS pH 7.4, 1% BSA, 0.005% Tween 20, 0.01% Triton X-100, and incubated overnight at 4° C. After washing, the lambody-antigen complexes were detected with ImmPRESS anti-mouse IgG-HRP and ImmPACT DAB peroxidase substrate, and counterstained with Hematoxylin (Vector Labs, Burlingame, Calif.).

Stained TMAs were scanned and scored using Aperio ScanScope XT instrument and the image analysis platform (Vista, Calif.). Digital images of stained tissue cores were analyzed by the Aperio Membrane v9 algorithm that reports for each core the percentage of positive membrane staining and average intensity in 4 categories: 0 (% negative cells), 1 (% low intensity), 2 (% medium intensity) and 3 (% high intensity). Arbitrary threshold for negative staining was set based on values of normal lung tissue. Samples from categories 0 and 1 were merged and arbitrary ranked as negative staining, and samples from categories 2 and 3 were merged and arbitrary ranked as positive staining. The association between positive staining with VLRB.aGPA.23 and patient clinical outcome was estimated by the method Kaplan-Meier. The Mantel-Cox log-rank test was used to calculate univariate correlation. Clinical diagnosis of samples was according to the TMA datasheet provided by IMGENEX.

Glycan Array.

For glycan array profiling, the fusion proteins VLR-B.aGPA.23-GCN4-biotin and VLRB.2D-GCN4-biotin were used, with a lysozyme binding clone (Tasumi et al., 2009) that served as a control. These lambodies were biotinylated via Maleimide-PEG$_2$-Biotin (Pierce), yielding about 2 moles biotin per mole protein. For the CFG array, Version 5.0 of the printed array was screened at three dilutions of the lambody: 2, 20 and 200 µg/mL, following their protocol that is available via the website that includes "functionalglycomics.org" in the URL after "www."

For the neoglycoprotein microarray (Oyelaran et al., 2009; Campbell et al., 2010) VLRB.aGPA.23 was screened at three dilutions of the lambody: 1, 10 and 100 µg/mL. Briefly, arrays were blocked with 3% BSA in PBS at 4° C. overnight and then VLRB.aGPA.23 was incubated on the array in fresh 1% BSA in PBST at 25° C. for 2 hours. Slides were washed with PBST and then bound VLRB.aGPA.23 was detected with Cy3-labeled Streptavidin (Invitrogen) at a 1:500 dilution in fresh 1% BSA in PBS at 25° C. for 1 hour. The glycan microarrays were scanned using GenePix Pro (Molecular Devices) at a PMT setting of 520, and data for each array component was averaged over 2 spots.

Surface Plasmon Resonance.

All SPR binding experiments were performed using Biacore T200 (GE Healthcare). The running and sample buffer was HBS-EP+ (10 mM HEPES, pH 7.4, 150 mM NaCl, 3 mM EDTA, 0.05% Polysorbate 20). All measurements were performed at 25° C. Anti-His antibody (His capture kit, GE Healthcare) was immobilized by amine coupling to Sensor Chip CM5. VLRB.aGPA.23 and Mut. 10 were diluted to 10 µg/mL and injected in each cycle at 10 µL/min for 30 seconds, to capture approximately 300 RU. The three antigens (aGPA, BG-H3-PAA, and TFα-PAA) were serially diluted in HBS-EP+ from 40 nM to 156 pM and injected at a flow rate of 30 µL/min. Regeneration of the anti-His surface was accomplished using a 60 second injection of 10 mM glycine-HCl pH 1.5. The reference subtracted SPR binding curves were blank subtracted, and curve fitting was performed with a 1:1 model to obtain kinetic parameters using the Biacore T200 Evaluation software.

Sequences
VLRB.aGPA.23 nucleotide sequence
(SEQ ID NO: 1)
```
GCATGTCCCTCGCAGTGTTCGTGCTCAGGGACAGAAGTGAACTGTGCAGG

GAAAAGCCTCGCGTCTGTGCCTGCAGGAATCCCCACCACAACGCGAGTGC

TGTATTTGAACAGCAATCAGATCACGAAGCTCGAGCCCGGGGTGTTTGAC

CGCCTGGCGAATTTGAGGGAGCTTCATCTGTGGGGGAACCAGCTGGTGTC

TCTTCCCCCTGGGGTGTTTGACAATCTGGCAAATCTGGAGAAGCTGTGGT

TGAACAGCAACCAGCTGACCTCTCTCCCCGCTGGGCTGTTTGATCGCCTG

GTGAATCTGGAGCATCTGGGTTTGTGCTGTATGAAGCTCACAGAGCTGCC

CAGTGGCGCATTTGACAAACTCACCCGGCTGAAGCAGTTGGGTCTGGACC

AGAATCAACTGAAGAGCATCCCTGACGGCGCGTTCGCTCGTCTCCCGAGC

CTCACCCACGTGTGGCTCCACACCAACCCCTGGGACTGTCAGTGCACGGA

CATCCTCTACTTGAGTGGCTGGGTCGCTCAGCACTCGAGCATCGTGGGTG

AGGGGTGGCCATGGAGGCACAGTCCAGACAGCGCCAAGTGCTCTGGTACT

AATACCCCCGTCCGTGCGGTCACCGAGGCCAGCACTAGCCCCTCGAAATG

CCCA
```

VLRB.aGPA.23 amino acid sequence
(SEQ ID NO: 2)
```
ACPSQCSCSGTEVNCAGKSLASVPAGIPTTTRVLYLNSNQITKLEPGVFD

RLANLRELHLWGNQLVSLPPGVFDNLANLEKLWLNSNQLTSLPAGLFDRL

VNLEHLGLCCMKLTELPSGAFDKLTRLKQLGLDQNQLKSIPDGAFARLPS

LTHVWLHTNPWDCQCTDILYLSGWVAQHSSIVGEGWPWRHSPDSAKCSGT

NTPVRAVTEASTSPSKCP
```

-continued
VLRB.gp120.4 nucleotide sequence
(SEQ ID NO: 3)
GCATGTCCCTCGCAGTGTTCGTGCTCAGGGACAACTGTGAACTGCCATAG

CAGACGCCTCACGTCTGTGCCTGCGGGAATCCCCACCACCACGCGTGTGC

TGTATTTGCACACCAATCAGATCACGAAGCTCGAGCCCGGGGTGTTTGAC

AGTCTGGTGAATCTGCAGCAGCTGTATATCAGTTGGAACCAGCTACAGGC

TCTACCCGTAGGGGTGTTTGACAAACTGACCCAGCTCACTCATCTGAGTC

TGTACAATAACCAGCTGAAGAGCATTCCCAGGGGCGCCTTTGATAACCTC

AAGAGCCTCACTCACATCTGGCTGGACAGAAACCCCTGGGACTGTCAATG

CACGGACATCCTCTACTTGAGTGGCTGGGTCGTTCAGCACTCGGGCATCG

TGCGGGAGCAGTGGACTGGGTCGTCGTGGTCCGTGAACCCAGACAGCGCC

AAGTGCGCTGGTACCAATACCCCCGTCCGTGCGGTCACCGAGGCCAGCAC

TAGCCCCTCGAAATGCCCA

VLRB.gp120.4 amino acid sequence
(SEQ ID NO: 4)
ACPSQCSCSGTTVNCHSRRLTSVPAGIPTTTRVLYLHTNQITKLEPGVFD

SLVNLQQLYISWNQLQALPVGVFDKLTQLTHLSLYNNQLKSIPRGAFDNL

KSLTHIWLDRNPWDCQCTDILYLSGWVVQHSGIVREQWTGSSWSVNPDSA

KCAGTNTPVRAVTEASTSPSKCP

VLRB.aGPA.23-AGmFc (diversity region (amino acids
8-225), then 6-His (amino acids 237-242) and
FLAG tags (amino acids 246-253), and then agly-
cosylated mouse IgG2a Fc (amino acids 256-485))
(SEQ ID NO: 5)
ASGATGAACPSQCSCSGTEVNCAGKSLASVPAGIPTTTRVLYLNSNQITK

LEPGVFDRLANLRELHLWGNQLVSLPPGVFDNLANLEKLWLNSNQLTSLP

AGLFDRLVNLEHLGLCCMKLTELPSGAFDKLTRLKQLGLDQNQLKSIPDG

AFARLPSLTHVWLHTNPWDCQCTDILYLSGWVAQHSSIVGEGWPWRHSPD

SAKCSGTNTPVRAVTEASTSPSKCPSGKGASGAAAAHHHHHHGSGDYKDD

DDKAGEPRGPTIKPCPPCKCPAPNLLGGPSVFIFPPKIKDVLMISLSPIV

TCVVVDVSEDDPDVQISWFVNNVEVHTAQTQTHREDYNGALRVVSALPIQ

HQDWMSGKEFKCKVNNKDLPAPIERTISKPKGSVRAPQVYVLPPPEEEMT

KKQVTLTCMVTDFMPEDIYVEWTNNGKTELNYKNTEPVLDSDGSYFMYSK

LRVEKKNWVERNSYSCSVVHEGLHNHHTTKSFSRTPGK

VLRB.aGPA.23-GCN4 (diversity region (amino acids
8-225), then 6-His (amino acids 237-242) and FLAG
tags (amino acids 246-253), human IgG1 linker
(amino acids 258-273), GCN4 leucine-zipper (amino
acids 275-307) terminating with additional GGC)
(SEQ ID NO: 6)
ASGATGAACPSQCSCSGTEVNCAGKSLASVPAGIPTTTRVLYLNSNQITK

LEPGVFDRLANLRELHLWGNQLVSLPPGVFDNLANLEKLWLNSNQLTSLP

AGLFDRLVNLEHLGLCCMKLTELPSGAFDKLTRLKQLGLDQNQLKSIPDG

AFARLPSLTHVWLHTNPWDCQCTDILYLSGWVAQHSSIVGEGWPWRHSPD

SAKCSGTNTPVRAVTEASTSPSKCPSGKGASGAAAAHHHHHHGSGDYKDD

DDKAGEPDKTHTCPPCPAPELLGGRMKQLEDKVEELLSKNYHLENEVARL

KKLVGERGGC

-continued
VLRB.gp120.4-AGmFc (diversity region (amino acids
8-180), then 6-His (amino acids 192-197) and FLAG
tags (amino acids 201-208), and then aglycosylated
mouse IgG2a Fc (amino acids 211-440))
(SEQ ID NO: 7)
ASGATGAACPSQCSCSGTTVNCHSRRLTSVPAGIPTTTRVLYLHTNQITK

LEPGVFDSLVNLQQLYISWNQLQALPVGVFDKLTQLTHLSLYNNQLKSIP

RGAFDNLKSLTHIWLDRNPWDCQCTDILYLSGWVVQHSGIVREQWTGSSW

SVNPDSAKCAGTNTPVRAVTEASTSPSKCPSGKGASGAAAAHHHHHHGSG

DYKDDDDKAGEPRGPTIKPCPPCKCPAPNLLGGPSVFIFPPKIKDVLMIS

LSPIVTCVVVDVSEDDPDVQISWFVNNVEVNTAQTQTHREDYNGALRVVS

ALPIQHQDWMSGKEFKCKVNNKDLPAPIERTISKPKGSVRAPQVYVLPPP

EEEMTKKQVTLTCMVTDFMPEDIYVEWTNNGKTELNYKNTEPVLDSDGSY

FMYSKLRVEKKNWVERNSYSCSVVHEGLHNHHTTKSFSRTPGK

VLRB.gp120.4-GCN4 (diversity region (amino acids
8-180), then 6-His (amino acids 192-197) and FLAG
tags (amino acids 201-208), human IgG1 linker
(amino acids 213-228), GCN4 leucine-zipper (amino
acids 230-262) terminating with additional GGC)
(SEQ ID NO: 8)
ASGATGAACPSQCSCSGTTVNCHSRRLTSVPAGIPTTTRVLYLHTNQITK

LEPGVFDSLVNLQQLYISWNQLQALPVGVFDKLTQLTHLSLYNNQLKSIP

RGAFDNLKSLTHIWLDRNPWDCQCTDILYLSGWVVQHSGIVREQWTGSSW

SVNPDSAKCAGTNTPVRAVTEASTSPSKCPSGKGASGAAAAHHHHHHGSG

DYKDDDDKAGEPDKTHTCPPCPAPELLGGRMKQLEDKVEELLSKNYHLEN

EVARLKKLVGERGGC

Example 2

Figure 9:
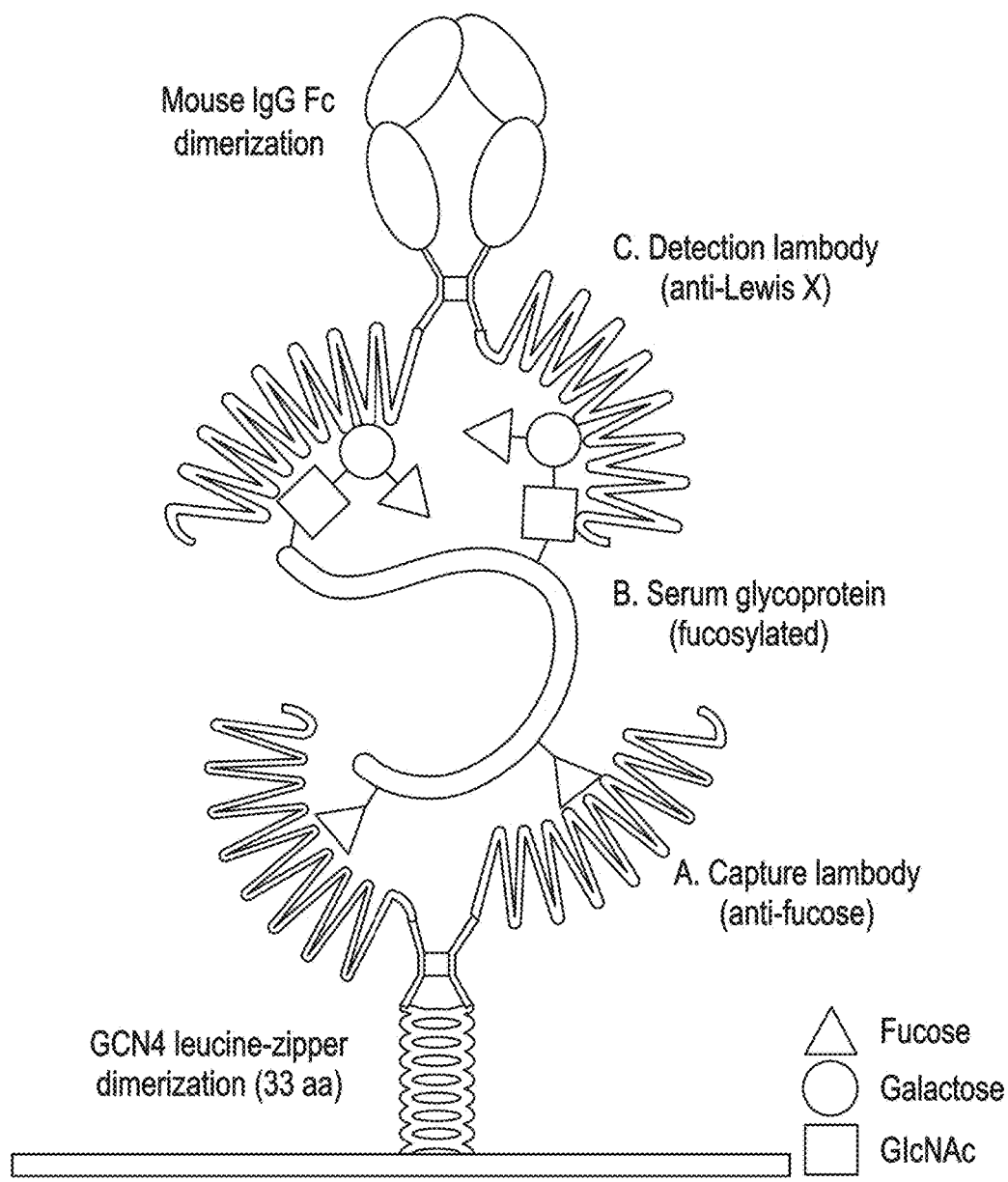
FIG. 9. Lambody-sandwich assay for detection of cancer-diagnostic antigens in serum glycoproteins. (A) Capture anti-fucose lambodies are immobilized on a solid support; (B) fucosylated glycoproteins from a cancer patient serum sample are captured through binding to two of the fucose structures; (C) the complex is overlaid with anti-Lewis X lambodies, which can be directly labeled for detection or detected by labeled anti-mouse IgG Fc antibodies, for example.

Lambodies display exquisite affinity and selectivity for glycans that is superior to that of most antibodies and lectins. Therefore, lambodies can be utilized to enhance the sensitivity and specificity of noninvasive cancer diagnostic assays. This can be done by lambody-sandwich assays, using immobilized lambodies to capture glycoprotein biomarkers from body fluid samples such as blood, urine or plasma. The captured glycoproteins are then overlaid with a second set of lambodies, for identification of cancer-specific complexes, as shown in FIG. 9. This is an example for the use of anti-fucose lambodies, but this assay can also be performed with sets of anti-NeuGc, or with any combination of anti-glycan lambodies. The assays can be performed in ELISA plates, or in printed lambody microarrays for high-throughput multiplexed analysis, or in biosensors for label-free detection. The lambody-sandwich assays can be used to predict early risk of cancer, for diagnosis, prognosis, and to monitor response to therapy.

Example 3

Figure 10:
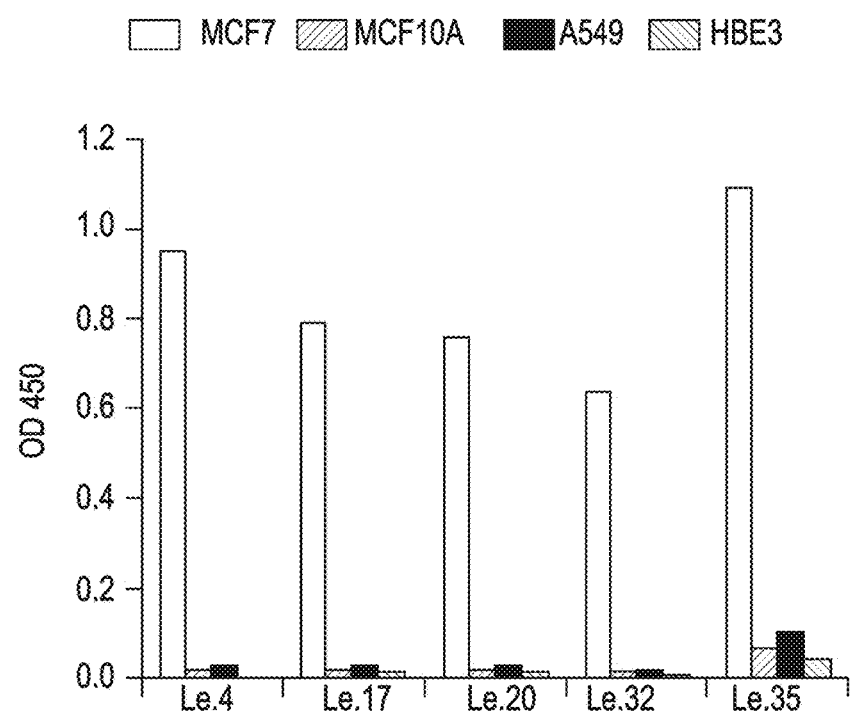
FIG. 10. Lambody capture ELISA of cell-surface proteins from breast cancer (MCF7; first column), normal breast (MCF10A; second column), lung cancer (A549; third column) and normal lung (HBE3; fourth column) cell-lines. Biotinylated probe proteins detected with streptavidin-HRP and TMB substrate.

The lambody-sandwich assay described in Example 2 can also be performed with sets of anti-NeuGc lambodies or lambody multimers that can distinguish body fluid samples of cancer patients from normal individuals. In a preliminary screen, five lambodies have been isolated that preferentially bind surface glycoproteins from a breast cancer cell line (MCF7), compared to matching normal breast (MCF10A), lung cancer (A549) and normal lung (HBE3) cell lines (FIG. 10). These lambodies display 17 to 72-fold higher binding values for breast cancer than for normal breast antigens, and they are also non-reactive with lung antigens. They were selected from the yeast surface-display library (Tasumi et al., 2009; Hong et al., 2012) using a combination of probes including synthetic glycans (Fucose, Lewis antigens and NeuGc) and cell-surface glycoproteins from breast cancer and normal cell lines, as well as the proteins they release in cultures (conditioned medium).

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. Each of the following references is among the references cited in this application:

Alder, M. N. et al. Diversity and function of adaptive immune receptors in a jawless vertebrate. *Science* 310, 1970-1973 (2005).

Alder, M. N. et al. Antibody responses of variable lymphocyte receptors in the lamprey. *Nat Immunol* 9, 319-327 (2008).

Almogren, A. et al. Anti-Thomsen-Friedenreich-Ag (anti-TF-Ag) potential for cancer therapy. *Front. Biosci. (Schol. Ed.)* 4, 840-863 (2012).

Blixt, O. et al. Printed covalent glycan array for ligand profiling of diverse glycan binding proteins. *Proc. Natl. Acad. Sci. U.S.A* 101, 17033-17038 (2004).

Boltz, K. W., Gonzalez-Moa, M. J., Stafford, P., Johnston, S. A., & Svarovsky, S. A. Peptide microarrays for carbohydrate recognition. *Analyst.* 134, 650-652 (2009).

Campbell, C. T. Zhang, Y. & Gildersleeve, J. C. Construction and Use of Glycan Microarrays. *Curr. Protocols Chem. Biol.* 2, 37-53 (2010).

Chaturvedi, R. et al. Tumor immunolocalization using 124 I-iodine-labeled JAA-F11 antibody to Thomsen-Friedenreich alpha-linked antigen. *Appl. Radiat. Isot.* 66, 278-287 (2008).

Corzana, F. et al. Serine versus threonine glycosylation: the methyl group causes a drastic alteration on the carbohydrate orientation and on the surrounding water shell. *J. Am. Chem. Soc.* 129, 9458-9467 (2007).

Cummings, R. D. The repertoire of glycan determinants in the human glycome. *Mol. Biosyst.* 5, 1087-1104 (2009).

Fujitani, N. et al. Expression of H type 1 antigen of ABO histo-blood group in normal colon and aberrant expressions of H type 2 and H type 3/4 antigens in colon cancer. *Glycoconj. J.* 17, 331-338 (2000).

Fujitani, N., Liu, Y., Okamura, T. & Kimura,H. Distribution of H type 1-4 chains of the ABO(H) system in different cell types of human respiratory epithelium. *J. Histochem. Cytochem.* 48, 1649-1656 (2000).

Han, B. W., Herrin, B. R., Cooper, M. D. & Wilson, I. A. Antigen recognition by variable lymphocyte receptors. *Science* 321, 1834-1837 (2008).

Hong, X., Ma, M. Z., Gildersleeve, J. C., Chowdhury, S., Barchi, J. J. Jr., Mariuzza, R. A., Murphy, M. B., Mao, L. & Pancer, Z. Sugar-Binding Proteins from Fish: Selection of High Affinity "Lambodies" That Recognize Biomedically Relevant Glycans. *ACS Chem. Biol.*, DOI: 10.1021/cb300399s (2012).

Hu, D., Tateno, H., Kuno, A., Yabe, R. & Hirabayashi, J. Directed evolution of lectins with a sugar-binding specificity for 6-sulfo-galactose. *J. Biol. Chem.* (2012).

Kannagi, R. Carbohydrate antigen sialyl Lewis a—its pathophysiological significance and induction mechanism in cancer progression. *Chang. Gung. Med. J.* 30, 189-209 (2007).

Karsten, U., Butschak, G., Stahn, R. & Goletz, S. A novel series of anti-human glycophorin A (CD235a) antibodies defining five extra- and intracellular epitopes. *Int. Immunopharmacol.* 10, 1354-1360 (2010).

Kim, H. M. et al. Structural diversity of the hagfish variable lymphocyte receptors. *J Biol Chem* 282, 6726-6732 (2007).

Le, P. J. et al. ABH and Lewis histo-blood group antigens in cancer. *APMIS.* 109, 9-31 (2001).

Li, Q., Anver, M. R., Li, Z., Butcher, D. O. & Gildersleeve, J. C. GalNAcalpha1-3Gal, a new prognostic marker for cervical cancer. *Int. J. Cancer* 126, 459-468 (2010).

Manimala, J. C., Roach, T. A., Li, Z. & Gildersleeve, J. C. High-throughput carbohydrate microarray analysis of 24 lectins. *Angew. Chem. Int. Ed. Engl.* 45, 3607-3610 (2006).

Manimala, J. C., Roach, T. A., Li, Z. & Gildersleeve, J. C. High-throughput carbohydrate microarray profiling of 27 antibodies demonstrates widespread specificity problems. *Glycobiology.* 17, 17C-23C (2007).

Moulaei, T. et al. Monomerization of viral entry inhibitor griffithsin elucidates the relationship between multivalent binding to carbohydrates and anti-HIV activity. *Structure* 18, 1104-1115 (2010).

Nagawa, F. et al. Antigen-receptor genes of the agnathan lamprey are assembled by a process involving copy choice. *Nat Immunol* 8: 206-213 (2007).

Oyelaran, O., Li, Q., Farnsworth, D. & Gildersleeve, J. C. Microarrays with varying carbohydrate density reveal distinct subpopulations of serum antibodies. *J. Proteome Res.* 8, 3529-3538 (2009).

Pancer, Z. et at. Variable lymphocyte receptors in hagfish. *Proc Natl Acad Sci USA* 102, 9224-9229 (2005).

Pancer, Z. et al. Somatic diversification of variable lymphocyte receptors in the agnathan sea lamprey. *Nature* 430, 174-180 (2004).

Pisano, A., Redmond, J. W., Williams, K. L., & Gooley, A. A. Glycosylation sites identified by solid-phase Edman degradation: O-linked glycosylation motifs on human glycophorin A. *Glycobiology.* 3, 429-435 (1993).

Powlesland, A. S. et al. Targeted glycoproteomic identification of cancer cell glycosylation. *Glycobiology.* 19, 899-909 (2009).

Ravn, P. et al. The Thomsen-Friedenreich disaccharide as antigen for in vivo tumor targeting with multivalent scFvs. *Cancer Immunol. Immunother.* 56, 1345-1357 (2007).

Rogozin, I. B. et al. Evolution and diversification of lamprey antigen receptors: Evidence for involvement of an AID-APOBEC family cytosine deaminase. *Nat Immunol* 8, 647-656 (2007).

Rittenhouse-Diakun, K. et al. Development and characterization of monoclonal antibody to T-antigen: (gal beta1-3GalNAc-alpha-0). *Hybridoma* 17, 165-173 (1998).

Sakai, K. et al. Isolation and characterization of antibodies against three consecutive Tn-antigen clusters from a phage library displaying human single-chain variable fragments. *J. Biochem.* 147, 809-817 (2010).

Sazinsky, S. L. et al., Aglycosylated immunoglobulin G1 variants productively engage activating Fc receptors. *Proc. Natl. Acad. Sci. USA* 105, 20167-72 (2008).

Stefan, N. et al. DARPins recognizing the tumor-associated antigen EpCAM selected by phage and ribosome display and engineered for multivalency. *J. Mol. Biol.* 413, 826-843 (2011).

Sun, W., Du, L. & Li, M. Aptamer-based carbohydrate recognition. *Curr. Pharm. Des.* 16, 2269-2278 (2010).

Tasumi, S. et al. High-affinity lamprey VLRA and VLRB monoclonal antibodies. *Proc. Natl. Acad. Sci. U.S.A* 106, 12891-12896 (2009).

Varki, A., Kannagi, R. & Toole, B. P. Glycosylation Changes in Cancer in In: *Essentials of Glycobiology* (Varki, A., Cummings, R. D., Esko, J. D., Freeze, H. H., Stanley, P., Bertozzi, C. R., Hart, G. W. & Etzler, M. E., eds.). Cold Spring Harbor Laboratory Press, Cold Spring Harbor (N. Y.) (2009). Chapter 44.

Wyatt, R. et al. The antigenic structure of the HIV gp120 envelope glycoprotein. *Nature* 393, 705-711 (1998).

What is claimed is:

1. A lambody, wherein the lambody comprises a first recombinant lambody subunit and a second recombinant lambody subunit, wherein each recombinant lambody subunit is a fusion protein consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, wherein the lambody subunits are dimerized via their multimerization domains, and wherein the lambody exhibits binding specificity for a glycan, glycolipid or glycoprotein.

2. The lambody of claim 1, wherein the VLR diversity regions of the first and second recombinant lambody subunits have identical amino acid sequences.

3. The lambody of claim 1, wherein the VLR diversity regions of the first and second recombinant lambody subunits have different amino acid sequences.

4. The lambody of claim 1, wherein the lambody exhibits a binding affinity ($K_D$) of at least about $1 \times 10^{-7}$ M for a target against which it exhibits binding specificity.

5. The lambody of claim 1, wherein the multimerization domain is selected from the group consisting of a yeast leucine zipper dimerization domain, a partial antibody hinge region and leucine zipper dimerization domain, a coil-coiled dimerization peptide, and an antibody Fc fragment.

6. A lambody multimer, wherein the lambody multimer comprises three or more multimerized recombinant lambody subunits, wherein the recombinant lambody subunits are each fusion proteins consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, wherein the lambody subunits are multimerized via their multimerization domains, and wherein the lambody multimer exhibits binding specificity for a glycan, glycolipid or glycoprotein.

7. The lambody multimer of claim 6, wherein the multimerization domain is selected from the group consisting of a yeast leucine zipper dimerization domain, a partial antibody hinge region and leucine zipper dimerization domain, a coil-coiled dimerization peptide, and an antibody Fc fragment.

8. A recombinant lambody subunit, wherein the recombinant lambody subunit is a fusion protein consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, wherein the lambody subunit exhibits binding specificity for a glycan, glycolipid or glycoprotein.

9. The recombinant lambody subunit of claim 8, wherein the multimerization domain is selected from the group consisting of a yeast leucine zipper dimerization domain, a partial antibody hinge region and leucine zipper dimerization domain, a coil-coiled dimerization peptide, and an antibody Fc fragment.

10. A method for isolating a glycan-bearing element from a sample, said method comprising (i) adhering a recombinant lambody subunit, lambody or lambody multimer to a support, (ii) contacting the support with a sample under conditions permitting binding of a glycan of the glycan-bearing element in the sample by a VLR diversity region of a recombinant lambody subunit, lambody or lambody multimer adhered to the support, (iii) washing unbound sample from the support, (iv) eluting the glycan-bearing element from the support, and (v) collecting the glycan-bearing element, wherein the recombinant lambody subunit is a fusion protein consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, and wherein the lambody subunit exhibits binding specificity for a glycan, glycolipid or glycoprotein;

wherein the lambody comprises a first recombinant lambody subunit and a second recombinant lambody subunit, wherein each recombinant lambody subunit is a fusion protein consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, wherein the lambody subunits are dimerized via their multimerization domains, and wherein the lambody exhibits binding specificity for a glycan, glycolipid or glycoprotein; and wherein the lambody multimer comprises three or more multimerized recombinant lambody subunits, wherein the recombinant lambody subunits are each fusion proteins consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, wherein the lambody subunits are multimerized via their multimerization domains, and wherein the lambody multimer exhibits binding specificity for a glycan, glycolipid or glycoprotein.

11. The method of claim 10, wherein the support is a bead in a column.

12. A method for detecting a glycan, glycolipid or glycoprotein in a biological sample from a subject, said method comprising (i) contacting a biological sample from a subject with a recombinant lambody subunit, lambody or lambody multimer under conditions permitting binding of the glycan, glycolipid or glycoprotein by a VLR diversity region of the recombinant lambody subunit, lambody or lambody multimer, and (ii) detecting binding by the VLR diversity region of the recombinant lambody subunit, lambody or lambody multimer to the glycan, glycolipid or glycoprotein in the sample, wherein the recombinant lambody subunit is a fusion protein consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, and wherein the lambody subunit exhibits binding specificity for a glycan, glycolipid or glycoprotein;

wherein the lambody comprises a first recombinant lambody subunit and a second recombinant lambody subunit, wherein each recombinant lambody subunit is a fusion protein consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, wherein the lambody subunits are dimerized via their multimerization domains, and wherein the lambody exhibits binding specificity for a glycan, glycolipid or glycoprotein; and wherein the lambody multimer comprises three or more multimerized recombinant lambody subunits, wherein the recombinant lambody subunits are each fusion proteins consisting of a lamprey variable lymphocyte receptor (VLR) diversity region linked via an amide bond to a multimerization domain, wherein the VLR diversity region is SEQ ID NO:2, SEQ ID NO:4, or the variant of SEQ ID NO:2 with the five amino acid mutations S19N, S86G, H105R, K112M and T208S, said variant differing from SEQ ID NO:2 only by the five amino acid mutations, wherein the lambody subunits are multimerized via their multimerization domains, and wherein the lambody multimer exhibits binding specificity for a glycan, glycolipid or glycoprotein.

13. The method of claim 12, wherein the biological sample is one or more selected from the group consisting of a bodily fluid, secretion, excretion, cells, tissue, and tissue biopsy.

14. The method of claim 12, wherein the lambody subunit, lambody or lambody multimer is conjugated to a detectable label.

15. The method of claim 12, wherein the detecting comprises (i) adding to the sample a secondary binding moiety labeled with a label, wherein the secondary binding moiety binds the lambody subunit, lambody or lambody multimer, and (ii) assaying for the label.

* * * * *

SEQUENCE LISTING

```
<160> NUMBER OF SEQ ID NOS: 9

<210> SEQ ID NO 1
<211> LENGTH: 654
<212> TYPE: DNA
<213> ORGANISM: Artificial Sequence
<220> FEATURE:
<223> OTHER INFORMATION: Lamprey VLRB.aGPA.23 nucleotide sequence

<400> SEQUENCE: 1
gcatgtccct cgcagtgttc gtgctcaggg acagaagtga actgtgcagg gaaaagcctc      60
gcgtctgtgc ctgcaggaat ccccaccaca acgcgagtgc tgtatttgaa cagcaatcag     120
atcacgaagc tcgagcccgg ggtgtttgac cgcctggcga atttgaggga gcttcatctg     180 tggggaacc agctggtgtc tcttcccct ggggtgtttg acaatctggc aaatctggag      240
aagctgtggt tgaacagcaa ccagctgacc tctctcccg ctgggctgtt tgatcgcctg      300
gtgaatctgg agcatctggg tttgtgctgt atgaagctca cagagctgcc cagtggcgca     360
tttgacaaac tcacccggct gaagcagttg ggtctggacc agaatcaact gaagagcatc     420
cctgacggcg cgttcgctcg tctcccgagc ctcacccacg tgtggctcca caccaacccc     480
tgggactgtc agtgcacgga catcctctac ttgagtggct gggtcgctca gcactcgagc     540
atcgtgggtg aggggtggcc atggaggcac agtccagaca gcgccaagtg ctctggtact     600
aatacccccg tccgtgcggt caccgaggcc agcactagcc cctcgaaatg ccca           654

<210> SEQ ID NO 2
<211> LENGTH: 218
<212> TYPE: PRT
<213> ORGANISM: Artificial Sequence
<220> FEATURE:
<223> OTHER INFORMATION: Lamprey VLRB.aGPA.23 amino acid sequence

<400> SEQUENCE: 2

Ala Cys Pro Ser Gln Cys Ser Cys Ser Gly Thr Glu Val Asn Cys Ala
1               5                   10                  15

Gly Lys Ser Leu Ala Ser Val Pro Ala Gly Ile Pro Thr Thr Thr Arg
            20                  25                  30

Val Leu Tyr Leu Asn Ser Asn Gln Ile Thr Lys Leu Glu Pro Gly Val
        35                  40                  45

Phe Asp Arg Leu Ala Asn Leu Arg Glu Leu His Leu Trp Gly Asn Gln
    50                  55                  60

Leu Val Ser Leu Pro Pro Gly Val Phe Asp Asn Leu Ala Asn Leu Glu
65                  70                  75                  80

Lys Leu Trp Leu Asn Ser Asn Gln Leu Thr Ser Leu Pro Ala Gly Leu
                85                  90                  95

Phe Asp Arg Leu Val Asn Leu Glu His Leu Gly Leu Cys Cys Met Lys
            100                 105                 110
```

Leu Thr Glu Leu Pro Ser Gly Ala Phe Asp Lys Leu Thr Arg Leu Lys
            115                 120                 125

Gln Leu Gly Leu Asp Gln Asn Gln Leu Lys Ser Ile Pro Asp Gly Ala
        130                 135                 140

Phe Ala Arg Leu Pro Ser Leu Thr His Val Trp Leu His Thr Asn Pro
145                 150                 155                 160

Trp Asp Cys Gln Cys Thr Asp Ile Leu Tyr Leu Ser Gly Trp Val Ala
                165                 170                 175

Gln His Ser Ser Ile Val Gly Glu Gly Trp Pro Trp Arg His Ser Pro
            180                 185                 190

Asp Ser Ala Lys Cys Ser Gly Thr Asn Thr Pro Val Arg Ala Val Thr
        195                 200                 205

Glu Ala Ser Thr Ser Pro Ser Lys Cys Pro
    210                 215

<210> SEQ ID NO 3
<211> LENGTH: 519
<212> TYPE: DNA
<213> ORGANISM: Artificial Sequence
<220> FEATURE:
<223> OTHER INFORMATION: Lamprey VLRB.gp120.4 nucleotide sequence

<400> SEQUENCE: 3
gcatgtccct cgcagtgttc gtgctcaggg acaactgtga actgccatag cagacgcctc      60
acgtctgtgc ctgcgggaat ccccaccacc acgcgtgtgc tgtatttgca caccaatcag     120
atcacgaagc tcgagcccgg ggtgtttgac agtctggtga atctgcagca gctgtatatc     180
agttggaacc agctacaggc tctacccgta ggggtgtttg acaaactgac ccagctcact     240
catctgagtc tgtacaataa ccagctgaag agcattccca ggcgcgcctt tgataacctc     300
aagagcctca ctcacatctg gctggacaga aaccctggg actgtcaatg cacggacatc     360
ctctacttga gtggctgggt cgttcagcac tcgggcatcg tgcgggagca gtggactggg     420
tcgtcgtggt ccgtgaaccc agacagcgcc aagtgcgctg gtaccaatac ccccgtccgt     480
gcggtcaccg aggccagcac tagcccctcg aaatgccca                            519

<210> SEQ ID NO 4
<211> LENGTH: 173
<212> TYPE: PRT
<213> ORGANISM: Artificial Sequence
<220> FEATURE:
<223> OTHER INFORMATION: Lamprey VLRB.gp120.4 amino acid sequence

<400> SEQUENCE: 4

Ala Cys Pro Ser Gln Cys Ser Cys Ser Gly Thr Thr Val Asn Cys His
1               5                   10                  15

Ser Arg Arg Leu Thr Ser Val Pro Ala Gly Ile Pro Thr Thr Thr Arg
            20                  25                  30

Val Leu Tyr Leu His Thr Asn Gln Ile Thr Lys Leu Glu Pro Gly Val
        35                  40                  45

Phe Asp Ser Leu Val Asn Leu Gln Gln Leu Tyr Ile Ser Trp Asn Gln
    50                  55                  60

Leu Gln Ala Leu Pro Val Gly Val Phe Asp Lys Leu Thr Gln Leu Thr
65                  70                  75                  80

His Leu Ser Leu Tyr Asn Asn Gln Leu Lys Ser Ile Pro Arg Gly Ala
                85                  90                  95

Phe Asp Asn Leu Lys Ser Leu Thr His Ile Trp Leu Asp Arg Asn Pro
            100                 105                 110

```
Trp Asp Cys Gln Cys Thr Asp Ile Leu Tyr Leu Ser Gly Trp Val Val
            115                 120                 125

Gln His Ser Gly Ile Val Arg Glu Gln Trp Thr Gly Ser Ser Trp Ser
        130                 135                 140

Val Asn Pro Asp Ser Ala Lys Cys Ala Gly Thr Asn Thr Pro Val Arg
145                 150                 155                 160

Ala Val Thr Glu Ala Ser Thr Ser Pro Ser Lys Cys Pro
                165                 170

<210> SEQ ID NO 5
<211> LENGTH: 488
<212> TYPE: PRT
<213> ORGANISM: Artificial Sequence
<220> FEATURE:
<223> OTHER INFORMATION: VLRB.aGPA.23-AGmFc lambody subunit

<400> SEQUENCE: 5

Ala Ser Gly Ala Thr Gly Ala Ala Cys Pro Ser Gln Cys Ser Cys Ser
1               5                   10                  15

Gly Thr Glu Val Asn Cys Ala Gly Lys Ser Leu Ala Ser Val Pro Ala
            20                  25                  30

Gly Ile Pro Thr Thr Thr Arg Val Leu Tyr Leu Asn Ser Asn Gln Ile
        35                  40                  45

Thr Lys Leu Glu Pro Gly Val Phe Asp Arg Leu Ala Asn Leu Arg Glu
    50                  55                  60

Leu His Leu Trp Gly Asn Gln Leu Val Ser Leu Pro Pro Gly Val Phe
65                  70                  75                  80

Asp Asn Leu Ala Asn Leu Glu Lys Leu Trp Leu Asn Ser Asn Gln Leu
                85                  90                  95

Thr Ser Leu Pro Ala Gly Leu Phe Asp Arg Leu Val Asn Leu Glu His
            100                 105                 110

Leu Gly Leu Cys Cys Met Lys Leu Thr Glu Leu Pro Ser Gly Ala Phe
        115                 120                 125

Asp Lys Leu Thr Arg Leu Lys Gln Leu Gly Leu Asp Gln Asn Gln Leu
    130                 135                 140

Lys Ser Ile Pro Asp Gly Ala Phe Ala Arg Leu Pro Ser Leu Thr His
145                 150                 155                 160

Val Trp Leu His Thr Asn Pro Trp Asp Cys Gln Cys Thr Asp Ile Leu
                165                 170                 175

Tyr Leu Ser Gly Trp Val Ala Gln His Ser Ser Ile Val Gly Glu Gly
            180                 185                 190

Trp Pro Trp Arg His Ser Pro Asp Ser Ala Lys Cys Ser Gly Thr Asn
        195                 200                 205

Thr Pro Val Arg Ala Val Thr Glu Ala Ser Thr Ser Pro Ser Lys Cys
    210                 215                 220

Pro Ser Gly Lys Gly Ala Ser Gly Ala Ala Ala His His His His His
225                 230                 235                 240

His His Gly Ser Gly Asp Tyr Lys Asp Asp Asp Lys Ala Gly Glu
                245                 250                 255

Pro Arg Gly Pro Thr Ile Lys Pro Cys Pro Pro Cys Lys Cys Pro Ala
        260                 265                 270

Pro Asn Leu Leu Gly Gly Pro Ser Val Phe Ile Phe Pro Pro Lys Ile
    275                 280                 285

Lys Asp Val Leu Met Ile Ser Leu Ser Pro Ile Val Thr Cys Val Val
    290                 295                 300
```

Val Asp Val Ser Glu Asp Pro Asp Val Gln Ile Ser Trp Phe Val
305                 310                 315                 320

Asn Asn Val Glu Val His Thr Ala Gln Thr Gln Thr His Arg Glu Asp
            325                 330                 335

Tyr Asn Gly Ala Leu Arg Val Val Ser Ala Leu Pro Ile Gln His Gln
            340                 345                 350

Asp Trp Met Ser Gly Lys Glu Phe Lys Cys Lys Val Asn Asn Lys Asp
            355                 360                 365

Leu Pro Ala Pro Ile Glu Arg Thr Ile Ser Lys Pro Lys Gly Ser Val
370                 375                 380

Arg Ala Pro Gln Val Tyr Val Leu Pro Pro Glu Glu Glu Met Thr
385                 390                 395                 400

Lys Lys Gln Val Thr Leu Thr Cys Met Val Thr Asp Phe Met Pro Glu
                405                 410                 415

Asp Ile Tyr Val Glu Trp Thr Asn Asn Gly Lys Thr Glu Leu Asn Tyr
            420                 425                 430

Lys Asn Thr Glu Pro Val Leu Asp Ser Asp Gly Ser Tyr Phe Met Tyr
            435                 440                 445

Ser Lys Leu Arg Val Glu Lys Lys Asn Trp Val Glu Arg Asn Ser Tyr
450                 455                 460

Ser Cys Ser Val Val His Glu Gly Leu His Asn His His Thr Thr Lys
465                 470                 475                 480

Ser Phe Ser Arg Thr Pro Gly Lys
                485

<210> SEQ ID NO 6
<211> LENGTH: 310
<212> TYPE: PRT
<213> ORGANISM: Artificial Sequence
<220> FEATURE:
<223> OTHER INFORMATION: VLRB.aGPA.23-GCN4 lambody subunit

<400> SEQUENCE: 6

Ala Ser Gly Ala Thr Gly Ala Ala Cys Pro Ser Gln Cys Ser Cys Ser
1               5                   10                  15

Gly Thr Glu Val Asn Cys Ala Gly Lys Ser Leu Ala Ser Val Pro Ala
            20                  25                  30

Gly Ile Pro Thr Thr Thr Arg Val Leu Tyr Leu Asn Ser Asn Gln Ile
        35                  40                  45

Thr Lys Leu Glu Pro Gly Val Phe Asp Arg Leu Ala Asn Leu Arg Glu
    50                  55                  60

Leu His Leu Trp Gly Asn Gln Leu Val Ser Leu Pro Pro Gly Val Phe
65                  70                  75                  80

Asp Asn Leu Ala Asn Leu Glu Lys Leu Trp Leu Asn Ser Asn Gln Leu
                85                  90                  95

Thr Ser Leu Pro Ala Gly Leu Phe Asp Arg Leu Val Asn Leu Glu His
            100                 105                 110

Leu Gly Leu Cys Cys Met Lys Leu Thr Glu Leu Pro Ser Gly Ala Phe
        115                 120                 125

Asp Lys Leu Thr Arg Leu Lys Gln Leu Gly Leu Asp Gln Asn Gln Leu
    130                 135                 140

Lys Ser Ile Pro Asp Gly Ala Phe Ala Arg Leu Pro Ser Leu Thr His
145                 150                 155                 160

Val Trp Leu His Thr Asn Pro Trp Asp Cys Gln Cys Thr Asp Ile Leu
                165                 170                 175

Tyr Leu Ser Gly Trp Val Ala Gln His Ser Ser Ile Val Gly Glu Gly
            180                 185                 190

Trp Pro Trp Arg His Ser Pro Asp Ser Ala Lys Cys Ser Gly Thr Asn
        195                 200                 205

Thr Pro Val Arg Ala Val Thr Glu Ala Ser Thr Ser Pro Ser Lys Cys
    210                 215                 220

Pro Ser Gly Lys Gly Ala Ser Gly Ala Ala Ala His His His His
225                 230                 235                 240

His His Gly Ser Gly Asp Tyr Lys Asp Asp Asp Lys Ala Gly Glu
                245                 250                 255

Pro Asp Lys Thr His Thr Cys Pro Pro Cys Pro Ala Pro Glu Leu Leu
        260                 265                 270

Gly Gly Arg Met Lys Gln Leu Glu Asp Lys Val Glu Glu Leu Leu Ser
        275                 280                 285

Lys Asn Tyr His Leu Glu Asn Glu Val Ala Arg Leu Lys Lys Leu Val
        290                 295                 300

Gly Glu Arg Gly Gly Cys
305                 310

<210> SEQ ID NO 7
<211> LENGTH: 443
<212> TYPE: PRT
<213> ORGANISM: Artificial Sequence
<220> FEATURE:
<223> OTHER INFORMATION: VLRB.gp120.4-AGmFc lambody subunit

<400> SEQUENCE: 7

Ala Ser Gly Ala Thr Gly Ala Ala Cys Pro Ser Gln Cys Ser Cys Ser
1               5                   10                  15

Gly Thr Thr Val Asn Cys His Ser Arg Arg Leu Thr Ser Val Pro Ala
            20                  25                  30

Gly Ile Pro Thr Thr Thr Arg Val Leu Tyr Leu His Thr Asn Gln Ile
        35                  40                  45

Thr Lys Leu Glu Pro Gly Val Phe Asp Ser Leu Val Asn Leu Gln Gln
    50                  55                  60

Leu Tyr Ile Ser Trp Asn Gln Leu Gln Ala Leu Pro Val Gly Val Phe
65                  70                  75                  80

Asp Lys Leu Thr Gln Leu Thr His Leu Ser Leu Tyr Asn Asn Gln Leu
            85                  90                  95

Lys Ser Ile Pro Arg Gly Ala Phe Asp Asn Leu Lys Ser Leu Thr His
        100                 105                 110

Ile Trp Leu Asp Arg Asn Pro Trp Asp Cys Gln Cys Thr Asp Ile Leu
    115                 120                 125

Tyr Leu Ser Gly Trp Val Val Gln His Ser Gly Ile Val Arg Glu Gln
        130                 135                 140

Trp Thr Gly Ser Ser Trp Ser Val Asn Pro Asp Ser Ala Lys Cys Ala
145                 150                 155                 160

Gly Thr Asn Thr Pro Val Arg Ala Val Thr Glu Ala Ser Thr Ser Pro
            165                 170                 175

Ser Lys Cys Pro Ser Gly Lys Gly Ala Ser Gly Ala Ala Ala His
        180                 185                 190

His His His His Gly Ser Gly Asp Tyr Lys Asp Asp Asp Lys
    195                 200                 205

Ala Gly Glu Pro Arg Gly Pro Thr Ile Lys Pro Cys Pro Pro Cys Lys
210                 215                 220

Cys Pro Ala Pro Asn Leu Leu Gly Gly Pro Ser Val Phe Ile Phe Pro
225                 230                 235                 240

Pro Lys Ile Lys Asp Val Leu Met Ile Ser Leu Ser Pro Ile Val Thr
            245                 250                 255

Cys Val Val Val Asp Val Ser Glu Asp Asp Pro Asp Val Gln Ile Ser
        260                 265                 270

Trp Phe Val Asn Asn Val Glu Val His Thr Ala Gln Thr Gln Thr His
    275                 280                 285

Arg Glu Asp Tyr Asn Gly Ala Leu Arg Val Val Ser Ala Leu Pro Ile
290                 295                 300

Gln His Gln Asp Trp Met Ser Gly Lys Glu Phe Lys Cys Lys Val Asn
305                 310                 315                 320

Asn Lys Asp Leu Pro Ala Pro Ile Glu Arg Thr Ile Ser Lys Pro Lys
            325                 330                 335

Gly Ser Val Arg Ala Pro Gln Val Tyr Val Leu Pro Pro Pro Glu Glu
        340                 345                 350

Glu Met Thr Lys Lys Gln Val Thr Leu Thr Cys Met Val Thr Asp Phe
    355                 360                 365

Met Pro Glu Asp Ile Tyr Val Glu Trp Thr Asn Asn Gly Lys Thr Glu
370                 375                 380

Leu Asn Tyr Lys Asn Thr Glu Pro Val Leu Asp Ser Asp Gly Ser Tyr
385                 390                 395                 400

Phe Met Tyr Ser Lys Leu Arg Val Glu Lys Lys Asn Trp Val Glu Arg
            405                 410                 415

Asn Ser Tyr Ser Cys Ser Val Val His Glu Gly Leu His Asn His His
        420                 425                 430

Thr Thr Lys Ser Phe Ser Arg Thr Pro Gly Lys
    435                 440

<210> SEQ ID NO 8
<211> LENGTH: 265
<212> TYPE: PRT
<213> ORGANISM: Artificial Sequence
<220> FEATURE:
<223> OTHER INFORMATION: VLRB.gp120.4-GCN4 lambody sequence

<400> SEQUENCE: 8

Ala Ser Gly Ala Thr Gly Ala Ala Cys Pro Ser Gln Cys Ser Cys Ser
1               5                   10                  15

Gly Thr Thr Val Asn Cys His Ser Arg Arg Leu Thr Ser Val Pro Ala
            20                  25                  30

Gly Ile Pro Thr Thr Thr Arg Val Leu Tyr Leu His Thr Asn Gln Ile
        35                  40                  45

Thr Lys Leu Glu Pro Gly Val Phe Asp Ser Leu Val Asn Leu Gln Gln
    50                  55                  60

Leu Tyr Ile Ser Trp Asn Gln Leu Gln Ala Leu Pro Val Gly Val Phe
65                  70                  75                  80

Asp Lys Leu Thr Gln Leu Thr His Leu Ser Leu Tyr Asn Asn Gln Leu
            85                  90                  95

Lys Ser Ile Pro Arg Gly Ala Phe Asp Asn Leu Lys Ser Leu Thr His
        100                 105                 110

Ile Trp Leu Asp Arg Asn Pro Trp Asp Cys Gln Cys Thr Asp Ile Leu
    115                 120                 125

Tyr Leu Ser Gly Trp Val Val Gln His Ser Gly Ile Val Arg Glu Gln
130                 135                 140

```
Trp Thr Gly Ser Ser Trp Ser Val Asn Pro Asp Ser Ala Lys Cys Ala
145                 150                 155                 160

Gly Thr Asn Thr Pro Val Arg Ala Val Thr Glu Ala Ser Thr Ser Pro
                165                 170                 175

Ser Lys Cys Pro Ser Gly Lys Gly Ala Ser Gly Ala Ala Ala Ala His
            180                 185                 190

His His His His His Gly Ser Gly Asp Tyr Lys Asp Asp Asp Asp Lys
        195                 200                 205

Ala Gly Glu Pro Asp Lys Thr His Thr Cys Pro Pro Cys Pro Ala Pro
        210                 215                 220

Glu Leu Leu Gly Gly Arg Met Lys Gln Leu Glu Asp Lys Val Glu Glu
225                 230                 235                 240

Leu Leu Ser Lys Asn Tyr His Leu Glu Asn Glu Val Ala Arg Leu Lys
                245                 250                 255

Lys Leu Val Gly Glu Arg Gly Gly Cys
            260                 265

<210> SEQ ID NO 9
<211> LENGTH: 33
<212> TYPE: PRT
<213> ORGANISM: Saccharomyces cerevisiae

<400> SEQUENCE: 9

Arg Met Lys Gln Leu Glu Asp Lys Val Glu Glu Leu Leu Ser Lys Asn
1               5                   10                  15

Tyr His Leu Glu Asn Glu Val Ala Arg Leu Lys Lys Leu Val Gly Glu
            20                  25                  30

Arg
```